United States Patent
van Mullekom

(10) Patent No.: US 6,786,859 B2
(45) Date of Patent: Sep. 7, 2004

(54) MAGNETIC FIELD THERAPY

(75) Inventor: Arnoldus Petrus van Mullekom, Horsley Park (AU)

(73) Assignee: Advanced Diagnostic Development Pty. Ltd., Horsley Park (AU)

(*) Notice: Subject to any disclaimer, the term of this patent is extended or adjusted under 35 U.S.C. 154(b) by 44 days.

(21) Appl. No.: 10/219,984

(22) Filed: Aug. 16, 2002

(65) Prior Publication Data

US 2003/0045770 A1 Mar. 6, 2003

(30) Foreign Application Priority Data

Aug. 17, 2001 (AU) ............................................. PR7117

(51) Int. Cl.[7] .............................. A61N 2/00; A61N 1/00
(52) U.S. Cl. ............................................. 600/9; 600/13
(58) Field of Search ............................. 600/9, 13, 417, 600/424, 435; 128/897, 899

(56) References Cited

U.S. PATENT DOCUMENTS

| | | | |
|---|---|---|---|
| 4,993,413 A | | 2/1991 | McLeod et al. |
| 5,084,003 A | | 1/1992 | Susic |
| 5,318,025 A | * | 6/1994 | Dumoulin et al. ........... 600/417 |
| 5,480,373 A | | 1/1996 | Fischer et al. |
| 5,518,496 A | | 5/1996 | McLeod et al. |
| 5,527,259 A | | 6/1996 | Grace et al. |
| 5,544,665 A | * | 8/1996 | Litovitz et al. .............. 128/897 |
| 5,752,911 A | * | 5/1998 | Canedo et al. .................. 600/9 |
| 6,123,657 A | * | 9/2000 | Ishikawa et al. ................ 600/9 |
| 6,234,953 B1 | | 5/2001 | Thomas et al. |
| 6,364,824 B1 | | 4/2002 | Fitzsimmons |
| 6,402,678 B1 | | 6/2002 | Fischell et al. |
| 6,461,289 B1 | * | 10/2002 | Muntermann .................. 600/9 |
| 6,558,311 B1 | * | 5/2003 | Muntermann ................ 600/13 |

OTHER PUBLICATIONS

Www.electroherbalism.com, 1998.
International Program on Chemical Safety Environmental Health Criteria 69, published by WHO, 1987.
*Cell Membrane Biochemistry and Neurobiological Approach to Biomagnetism*, M.J. Azana & A Del Moral, 1994.

* cited by examiner

*Primary Examiner*—Eric F. Winakur
*Assistant Examiner*—Nikita R Veniaminov
(74) *Attorney, Agent, or Firm*—Jagtiani + Guttag

(57) ABSTRACT

An apparatus (1) for applying magnetic field treatment to a biological entity is disclosed. The apparatus has a signal generation unit (6) for generating an electrical treatment signal, and an induction coil mat (5), connected to said signal generation unit (6). A magnetic field is generated by the induction coil mat (5) in accordance with said electrical treatment signal. The electrical treatment signal comprises frequency components of approximately 300 Hz, 600 Hz, 800 Hz and 1,000 Hz in superposition. A further set of frequencies in the range between 2 Hz and 32 Hz can be added. These further frequencies are chosen in accordance with a desired treatment mode of operation.

17 Claims, 40 Drawing Sheets

40 Year Old Cancer Patient

60 Year Old Cancer Patient

65 Year Old Angina Sufferer
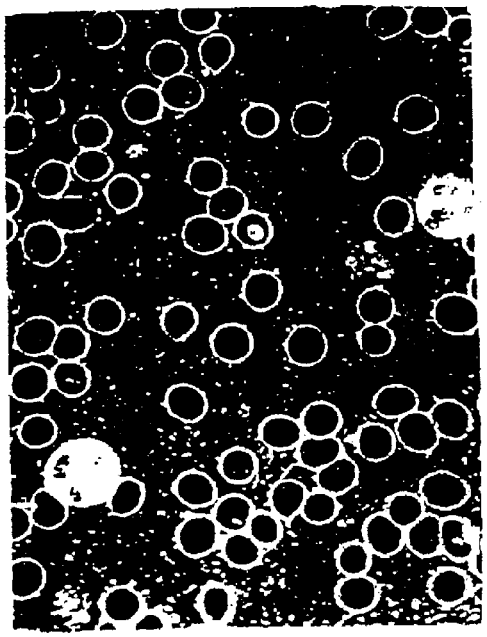
Fig. 20A                     Fig. 20B
75 Year Old Diabetic Patient
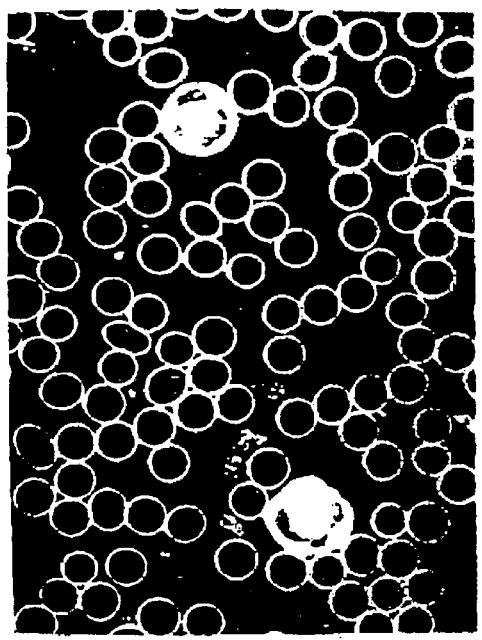 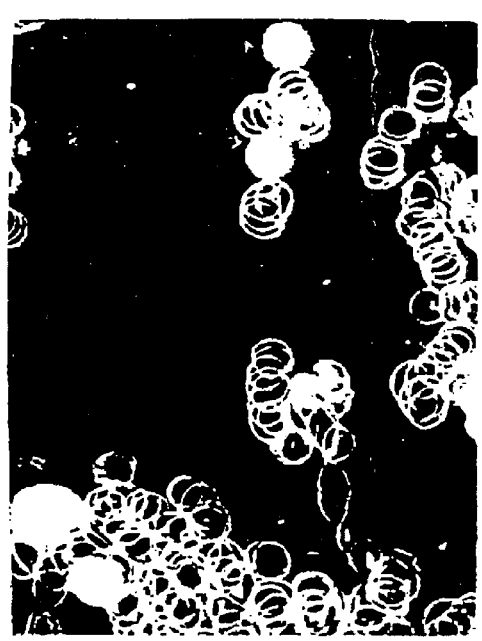
Fig. 21A                     Fig. 21B

30 YEAR OLD INFLUENZA SUFFERER

MAGNETIC FIELD THERAPY

TECHNICAL FIELD OF THE INVENTION

The present invention relates to a method and apparatus for applying magnetic field/s to a biological entity (such as humans and animals) as a means of therapy.

BACKGROUND ART

The application of magnetic fields to treat cells of the human or animal body has been proposed for a wide range of physiological conditions.

One example in the prior art, is the RONEFOR® Model 2, EL VX50 device that originated in Austria. A magnetic field which is pulsating at around 50 Hz is locally applied to the human body. Typically, this therapy is applied for 30 minutes at a time, twice a day. However, the required "intensity" (i.e. magnetic flux density) for this treatment is relatively high: 400–5,600 microteslas ($\mu$T) (equivalent to 4–56 Gauss).

Another example in the prior art, is the Quantron Resonance System® ("QRS®") manufactured by Magnavit AG of Liechtenstein, in which device a pulsing magnetic field is applied with an intensity of 15–30 $\mu$T. The electrical signal used to produce the magnetic field includes a base frequency of 200 Hz and further frequencies of 3 and 28 Hz. The signal is applied in a repeating cycle of 205 pulses over 4.9 ms followed by an interruption of 5 ms. The intensity is varied according to the required therapy. However, only around 30% of body cells are estimated to be able to be reached with this arrangement.

The present invention has as an object improved therapeutic performance over the prior art.

DISCLOSURE OF THE INVENTION

The invention discloses an apparatus for applying a thereapeutic magnetic field to a biological entity. The apparatus comprising a signal generation unit for generating an electrical treatment signal having a plurality of superimposed frequency components components of approximately 300 Hz, 600 Hz, 800 Hz and 1,000 Hz. An induction coil mat is connected to said signal generation unit, and generates a magnetic field in accordance with said electrical signal.

The invention further discloses a mthod for applying a therapeutic magnetic field to a biological entity (human or animal).

The fundamental frequency components discussed above are understood to be primarily responsible for initiating the biochemical processes within the body, for increasing cell membrane permeability and re-establishing normal potentials to damaged cells. In particular, these high frequency components are believed to be primarily responsible for providing an improved calcium cascade effect within the cells, where $Ca^{2+}$ ions penetrate cell membranes. These high frequency signals alone can provide beneficial treatment effects.

One or more relatively low frequency components, in the range 3 Hz to 32 Hz, can be added. These frequencies are chosen in accordance with a desired treatment mode of operation.

BRIEF DESCRIPTION OF THE DRAWINGS

FIGS. 17A and 17B, 18A and 18B, 19A and 19B, 20A and 20B, 21A and 21B, and 22A and 22b show results obtained in clinical trials;

DETAILED DESCRIPTION INCLUDING BEST MODE

Apparatus

Figure 1:
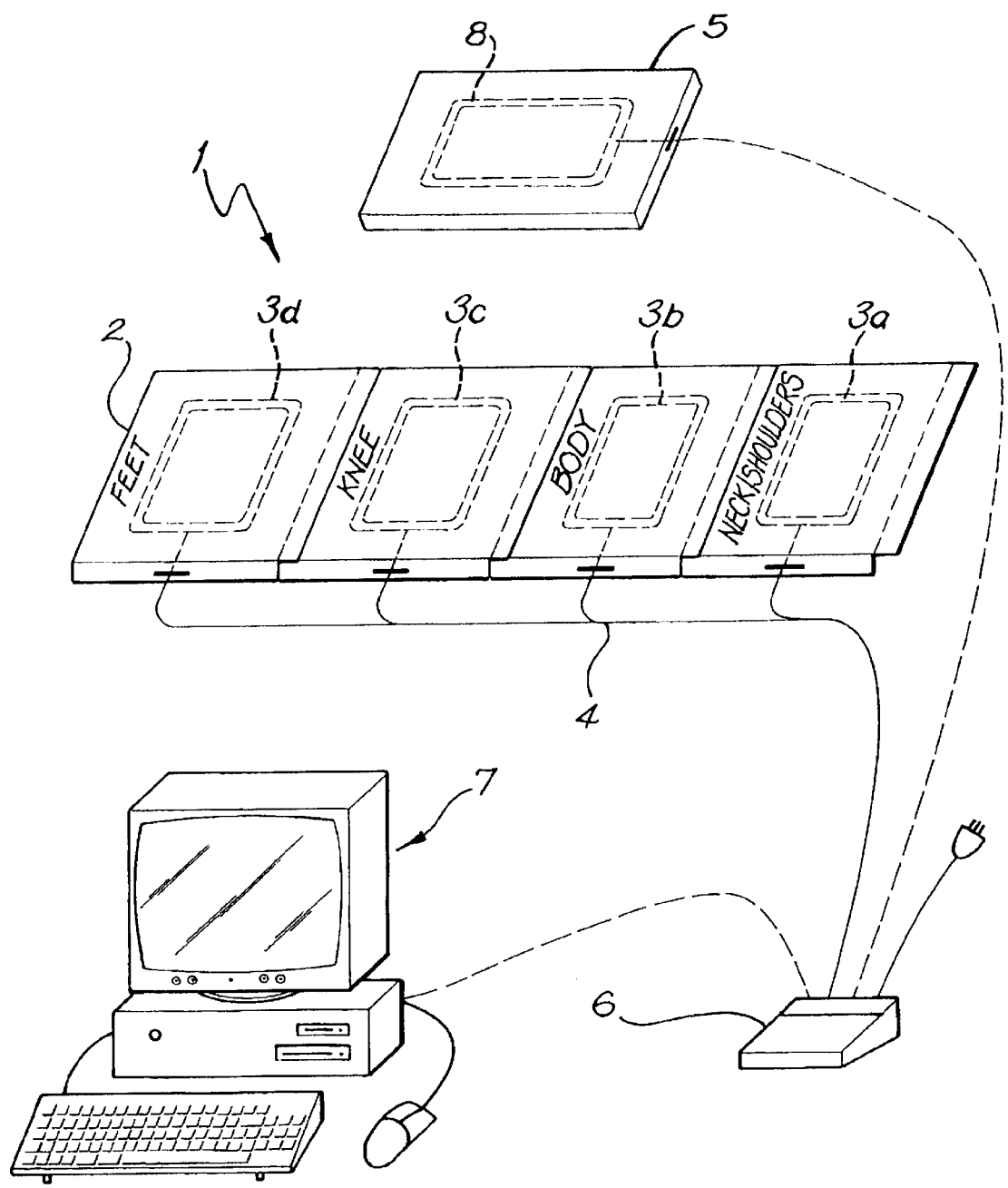
FIG. 1 is a schematic representation of the main functional components of a magnetic field therapy apparatus according to an embodiment of the present invention.

Referring to FIG. 1, a magnetic field therapy apparatus 1 includes a therapy control unit 6 connected to either a single-coil induction mat 5 or a multi-coil induction mat 2, depending upon the type and extent of magnetic therapy intended to be applied.

The therapy control unit 6 typically includes a microcontroller based system which provides a pulsing, electrical output which will be referred to as a "therapy" signal. The therapy signal is controlled in accordance with a desired field strength, determined by current flow, and a desired waveform characteristic (to be later described), to provide an excitation source for each of the mats 2, 5.

In a domestic context, the therapy control unit 6 typically includes an EEPROM memory chip in which to store operating and historical data. However, in a medical practice or therapist's context, the therapy control unit 6 can be connected to and communicate with a personal computer 7 to provide further management and record keeping facilities.

The single-coil mat 5 is made of foam rubber having a thickness of around 30 mm. The single-coil mat 5 includes an embedded, flat, air core induction coil 8a, which typically includes around 30–50 turns over a total length of around 10–100 m. In one specific example, the induction coil 8a has 35 turns providing a total length of 60 m, and is wound from a stranded conductor having a cross-sectional area (csa) between 0.5 $mm^2$ and 1 $mm^2$, and preferably 0.75 $mm^2$.

Figure 4:
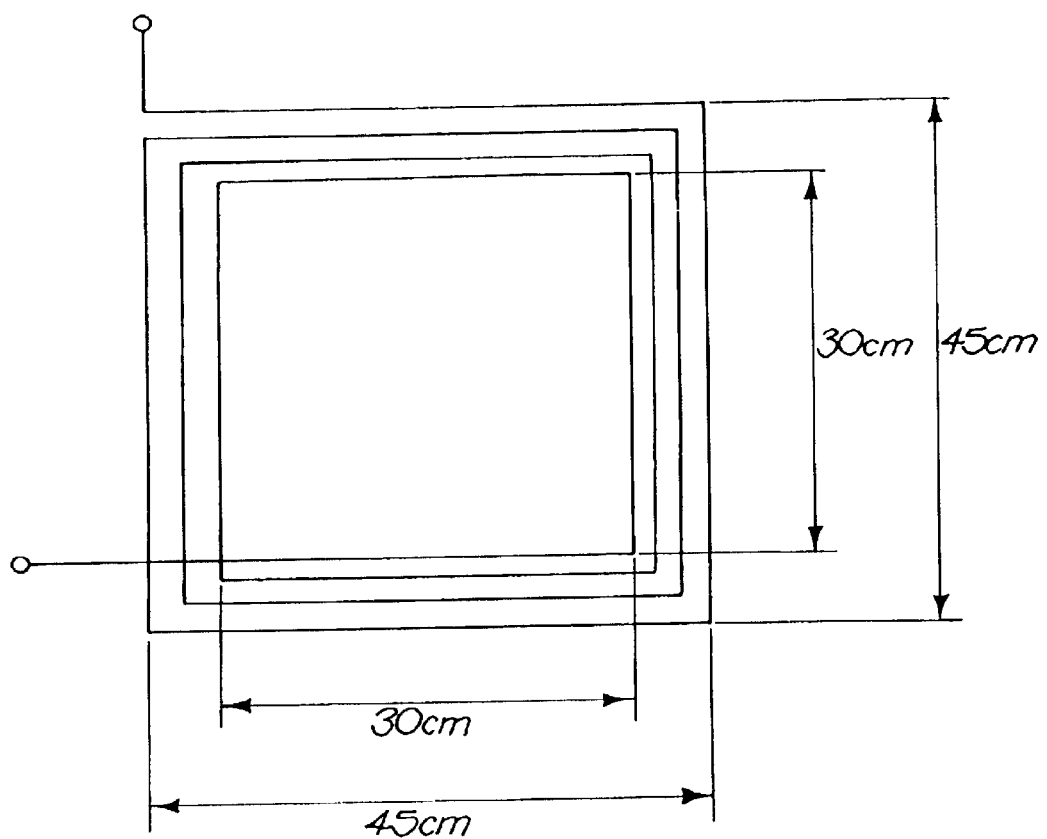
FIG. 4 is a schematic diagram of a coil used in the magnetic field therapy apparatus of FIGS. 1–3.

Referring to FIG. 4, an example of typical dimensions of an induction coil 8a is shown.

The single coil mat 5 is sufficiently flexible to be able to be wrapped around a human joint such as a knee, elbow or the like to thus enable localised therapy to be applied.

The multi-coil mat 2 is similarly constructed to the single-coil mat 5 although is embedded with four, rectangular, flat, air-core induction coils 3a–3d.

In one form of the multi-coil mat 2, the therapy control unit 6 provides a single source of excitation to each of the induction coils 3a–3d. However, in another embodiment of the multi-coil mat 2, each of the induction coils 3a–3d are separately connected to the therapy control unit 6 so as to be independently excitable. This enables a different field intensity and/or frequencies to be simultaneously applied to different parts of the user's body. For example, when lying down on the multi-coil mat 2, coil 3a can generate a lower intensity near the user's head and coil 3d can generate a higher intensity near the user's feet.

Magnetic Field Waveforms

The therapy control unit 6 synthesises the therapy signal $\mu_{AM}(t)$ which is used to excite the coils 3a to 3d and 8. The therapy signal $\mu_{AM}(t)$ is made up of a "basic" signal $\mu_T(t)$ and a "user" signal $\mu_M(t)$, which are superimposed (i.e. added) together with a form of amplitude scaling applied.

Figure 5:
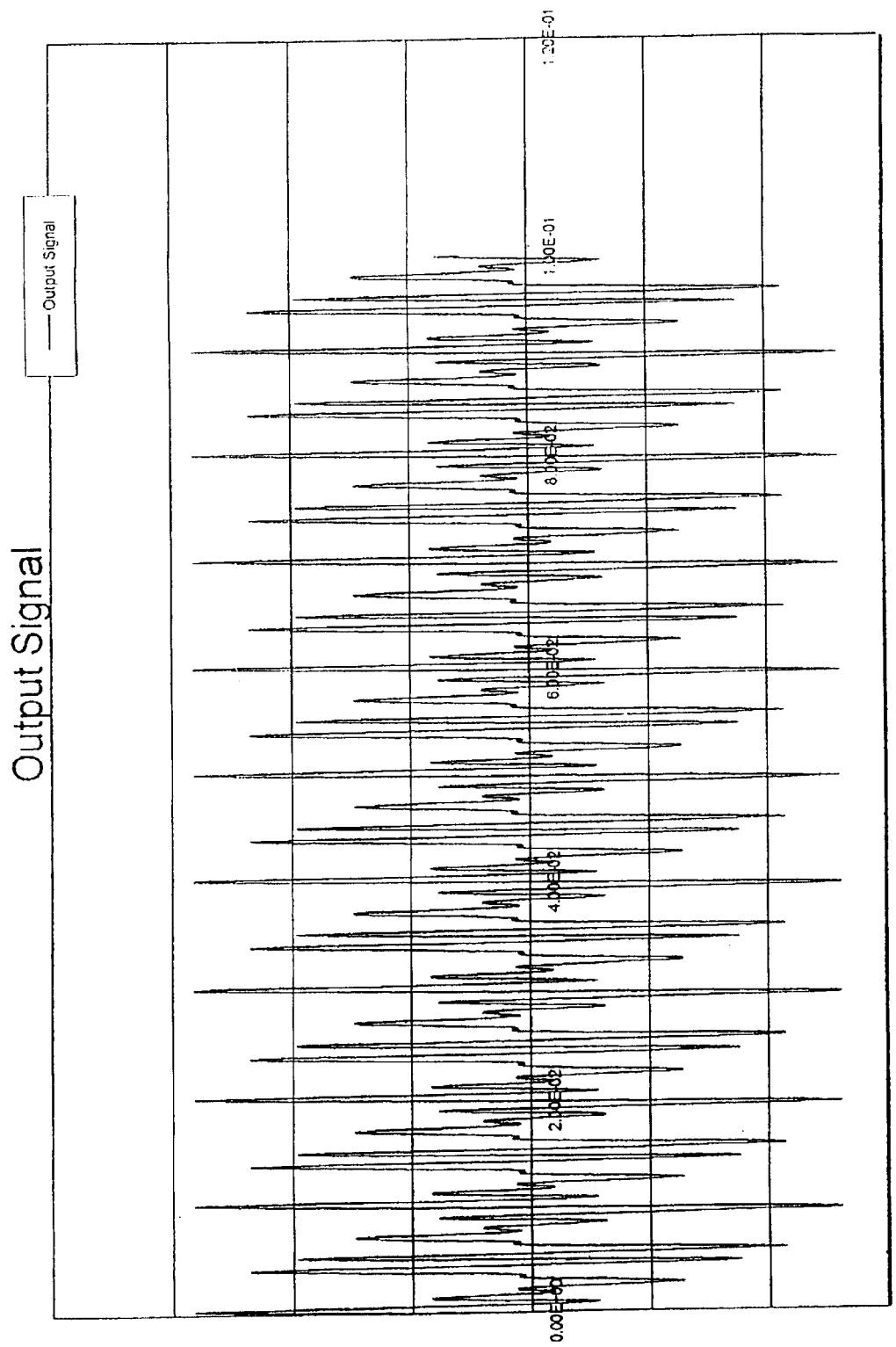
FIG. 5 is a time domain representation of a basic carrier signal used in the operation of the magnetic field therapy apparatus of FIGS. 1 to 3.

Referring now to FIG. 5, an example of the basic signal, $\mu_T(t)$, (or $V_{output}$) is shown, which includes the following four sinusoidal frequency components and a dc component (0 V in this case), in superposition:

| | |
|---|---|
| $f_1$ = | 300 Hz |
| $f_2$ = | 600 Hz |
| $f_3$ = | 800 Hz |
| $f_4$ = | 1000 Hz |

The fundamental "frequency" components of the basic signal discussed above are understood to be primarily responsible for initiating the biochemical processes within the body, for increasing cell membrane permeability and re-establishing normal potentials to damaged cells. In particular, these high frequency components are believed to be primarily responsible for providing an improved calcium cascade effect within the cells, where $Ca^{2+}$ ions penetrate cell membranes. These high frequency signals alone can provide beneficial treatment effects.

The "low frequency" component of the user signal is believed to be primarily responsible for providing a resonance effect by coinciding with the natural frequencies of the body (e.g. brain and nervous system activity and cell structures), and is specific for the treatment applied.

The relevant frequencies of the user signal $\mu_T(t)$ depends upon the nature of the therapy to be applied. The frequency of the user signal $\mu_T(t)$ is typically within the range of frequencies of the human electroencephalogram (EEG), or between 3 Hz to 32 Hz. The frequency bands of the human EEG are as follows:

| | |
|---|---|
| Beta band: | >13 Hz |
| Beta 1: | 14–18 Hz |
| Beta 2: | >18 Hz |
| Alpha band: | 8–13 Hz |
| Theta band: | 4–7 Hz |
| Delta band: | 0.5–3.5 Hz |

The user signal $\mu_M(t)$ is sinusoidal with an amplitude of 1 unit. This enables the user signal $\mu_M(t)$ to be weighted with an amplitude factor (A) between 20% to 100% to ensure that the current flow through each of the coils 3a–3d and 8, and resultant intensity of magnetic field generation, is maintained at a constant level for the duration of a therapy program.

The therapy signal $\mu_{AM}(t)$ includes a further scaling factor applied to the superimposed frequencies such that they are scaled back so that the intensity across the frequency range remains largely the same and below a maximum level.

It is believed by the inventor that a therapy signal $\mu_{AM}(t)$ composed in accordance with the above principles can provide at least similar benefits to those realised from prior art devices, but with generally lower field intensities. Lower field intensities are believed to provide a safer situation against adverse effects to the patients. Also, these lower intensities are more likely to conform to various regulatory standards.

Consistent with the basic principles expressed, a number of therapeutic programs, based on various frequencies and durations of user signals $\mu_M(t)$, combined with the basic signal $\mu_T(t)$, have been devised. Each of these programs are directed to specific physiological areas, as determined by testing, as follows:

1. Vitalisation/Blood Circulation,
2. Relaxation,
3. Vigilance/Activation,
4. Pain,
5. Relaxation and Revitalisation,
6. Sleep.

When treating for vitalisation or blood circulation, the user signal $\mu_M(t)$ is chosen to firstly activate frequencies in the beta band and thereafter frequencies in the alpha band.

When treating for pain, it should be taken into consideration that most patients will also be taking some form of analgesic drugs, which can cause artificial changes in the human EEG, for example:

(a) there can be an increase in theta activity (4–7 Hz), (b) a decrease in alpha activity (8–13 Hz) which is particularly the case when the drug ASS is taken, in which case the alpha rhythm is destroyed to a large extent, and (c) there can be an increase in beta 3 frequency (21–30 Hz), particularly with the use of the drug Pentazocin™.

The program concerned with relaxation and revitalisation (i.e. program 5), a combination of programs 2 and 3 are utilised.

When treating for sleep, the user signal $\mu_M(t)$ is chosen so that the percentage of the theta band is greater than 50%.

When treating for vigilance, generally the opposite to the sleep program is sought.

Waveform Sets

It is useful to now describe a set of waveforms that can be utilised in the respective therapeutic programs. The waveforms are characterised by an algebraic summing, as described above.

Figure 6A:
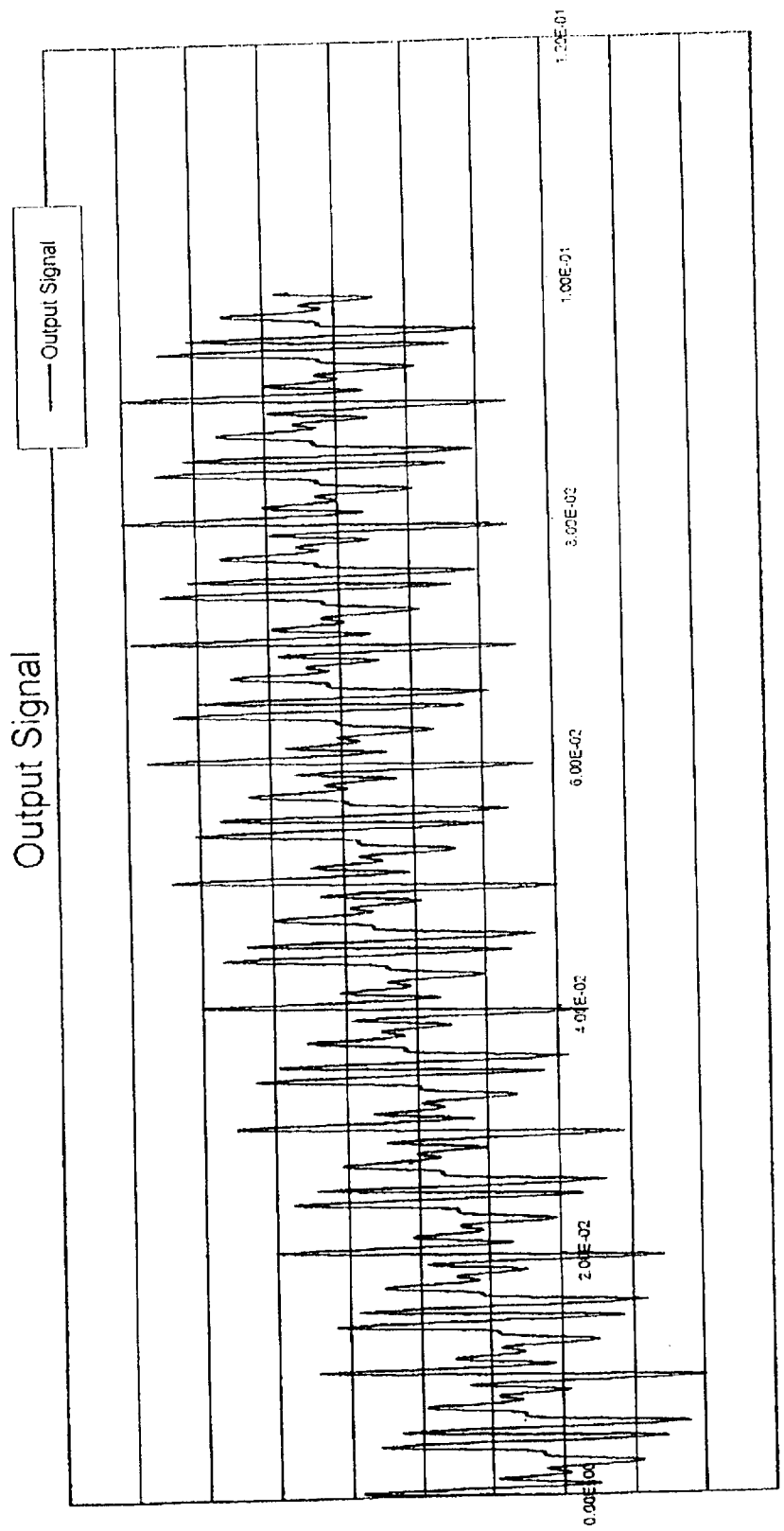
FIGS. 6A to 6C, 7A to 7C, 8A to 8C, 9A to 9C, 10A to 10C, 11A to 11C, 12A to 12C, 13A to 13C and 14A to 14C each illustrate a pair of time domain representations of a therapy signal used in the operation of the magnetic field therapy apparatus of FIGS. 1 to 3.

Referring to FIG. 6A, the therapy signal $\mu_{AM}(t)$ or $V_{output}$ includes a user signal $\mu_M(t)$ or $V_{var}$ having a frequency of 3 Hz and ampfact of 100%.

Figure 6B:
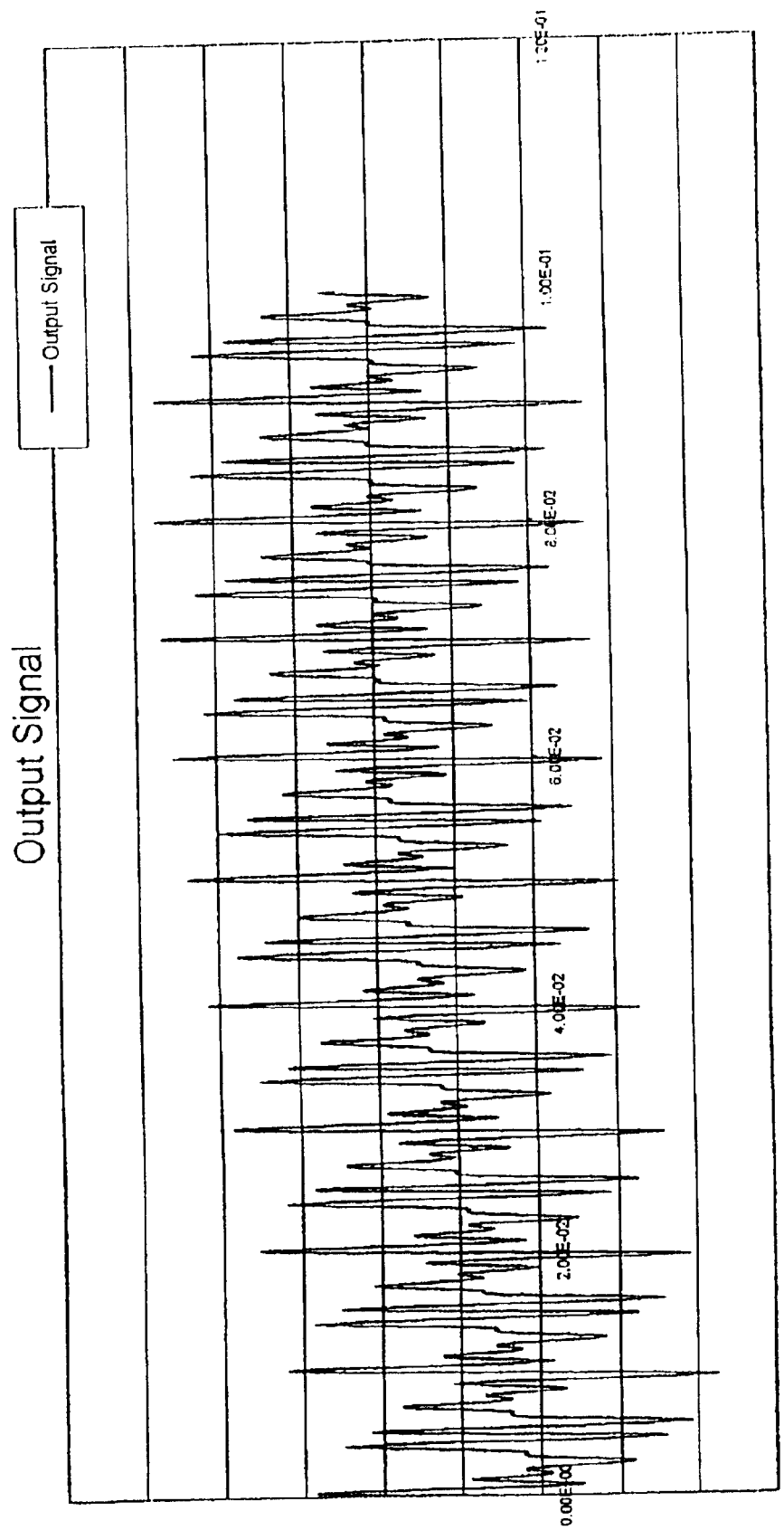
Figure 6C:
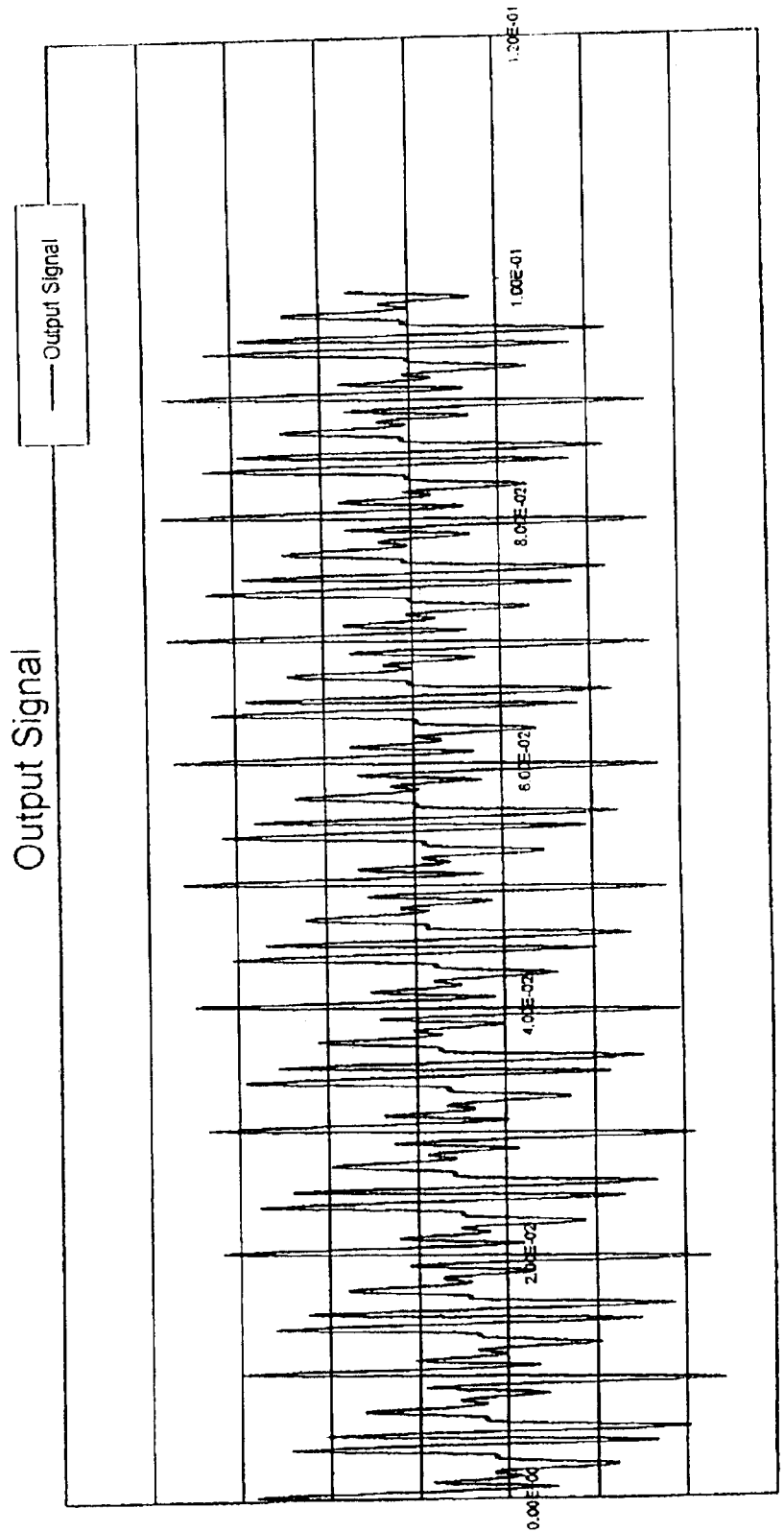

FIGS. 6B and 6C show graphs in a similar format to that of FIG. 6A, except that ampfact of the user signal is 60% and 30% respectively.

Figure 7A:
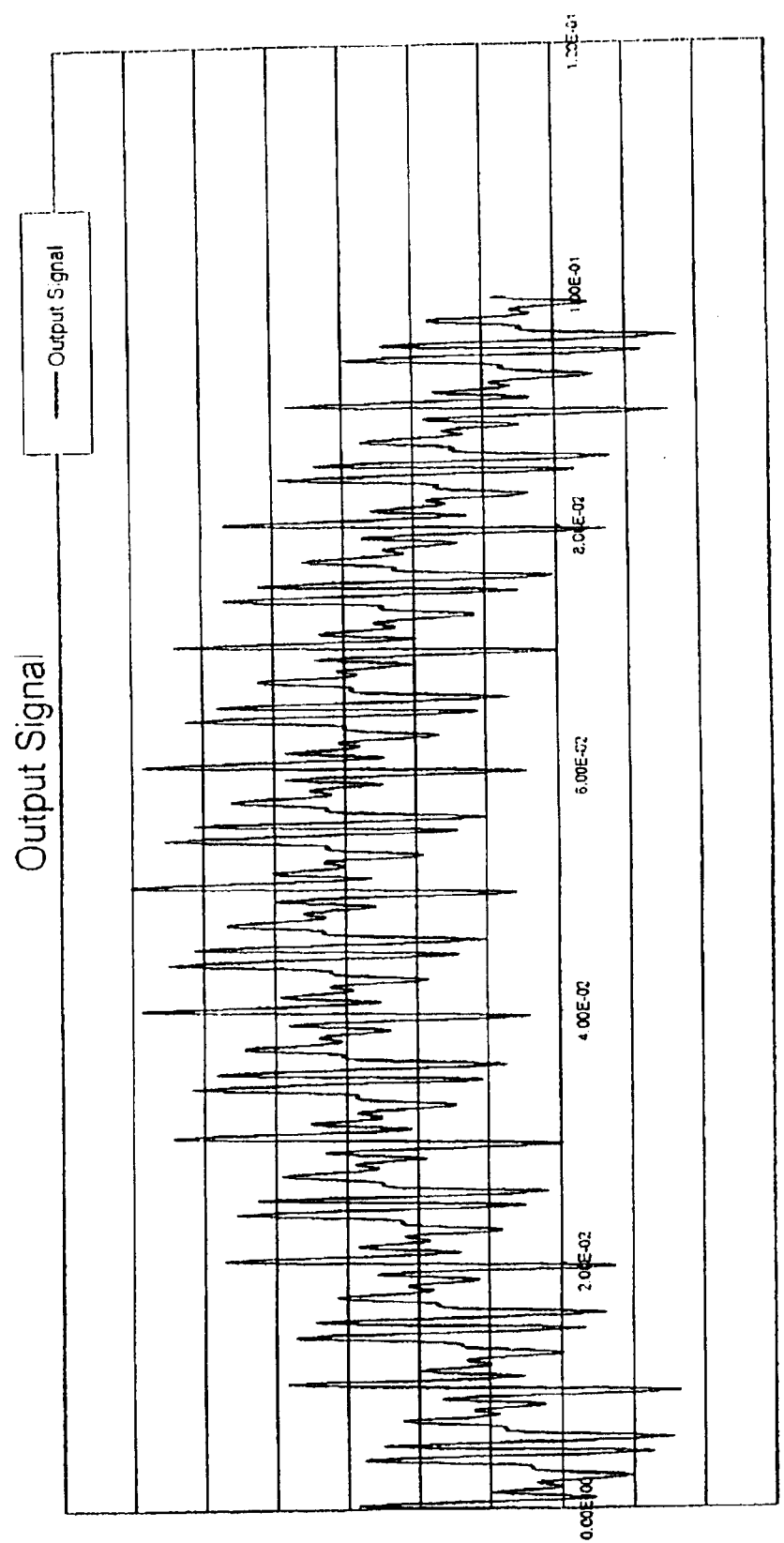
Figure 7B:
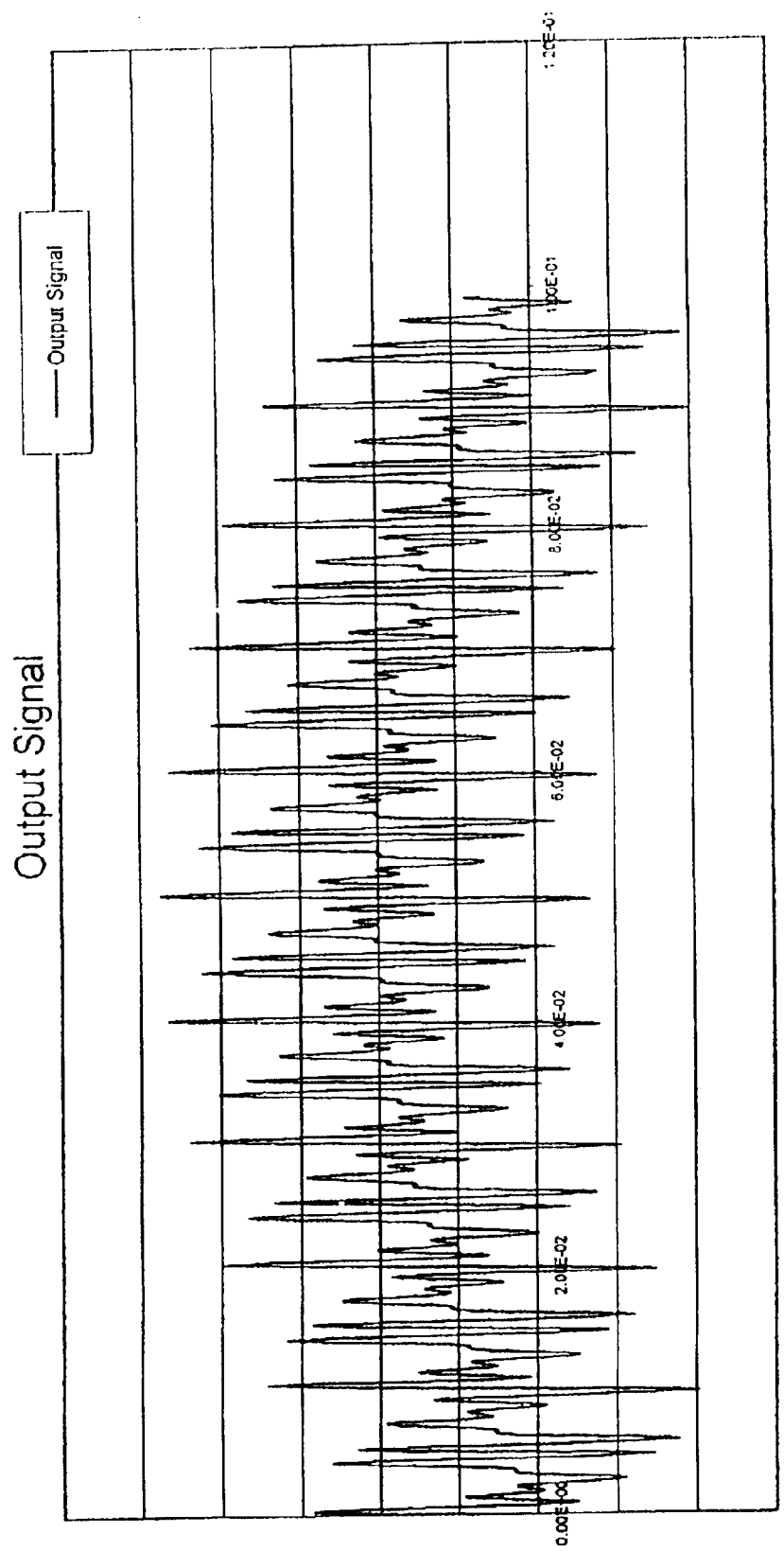
Figure 7C:
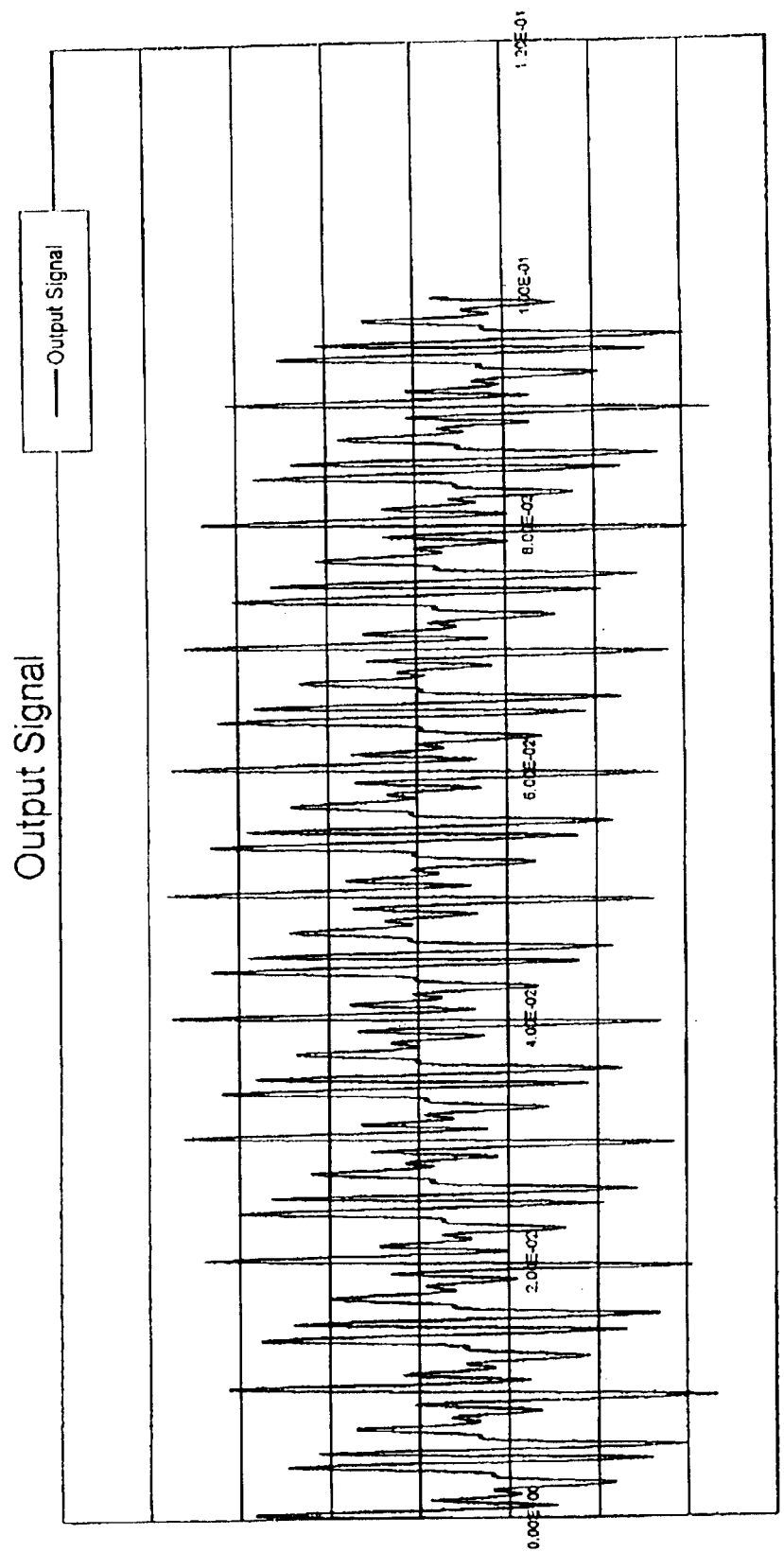

FIGS. 7A to 7C each show upper and lower graphs in a similar format to that of FIGS. 6A to 6C respectively, except that the frequency of the user signal is 5 Hz.

Figure 8A:
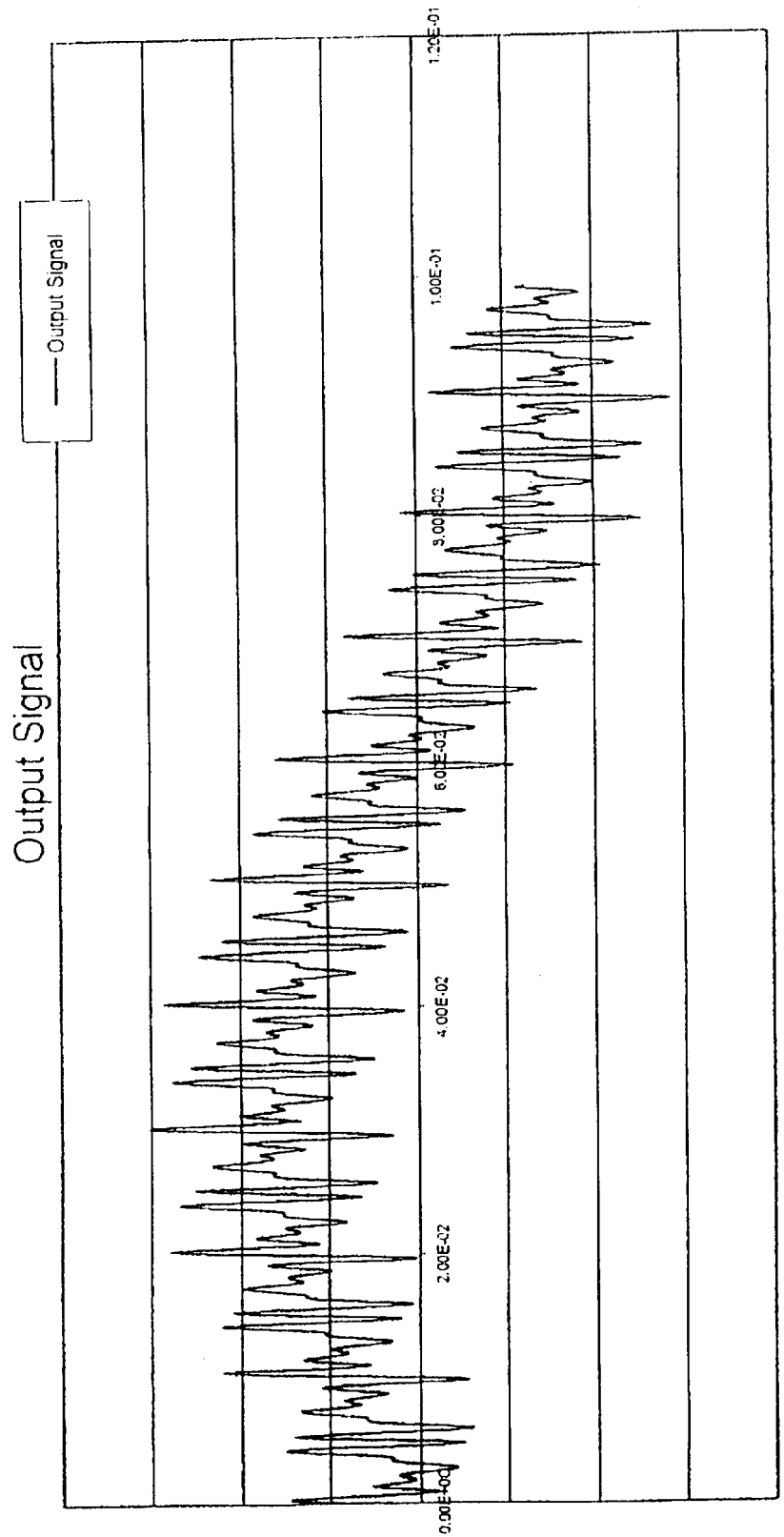
Figure 8B:
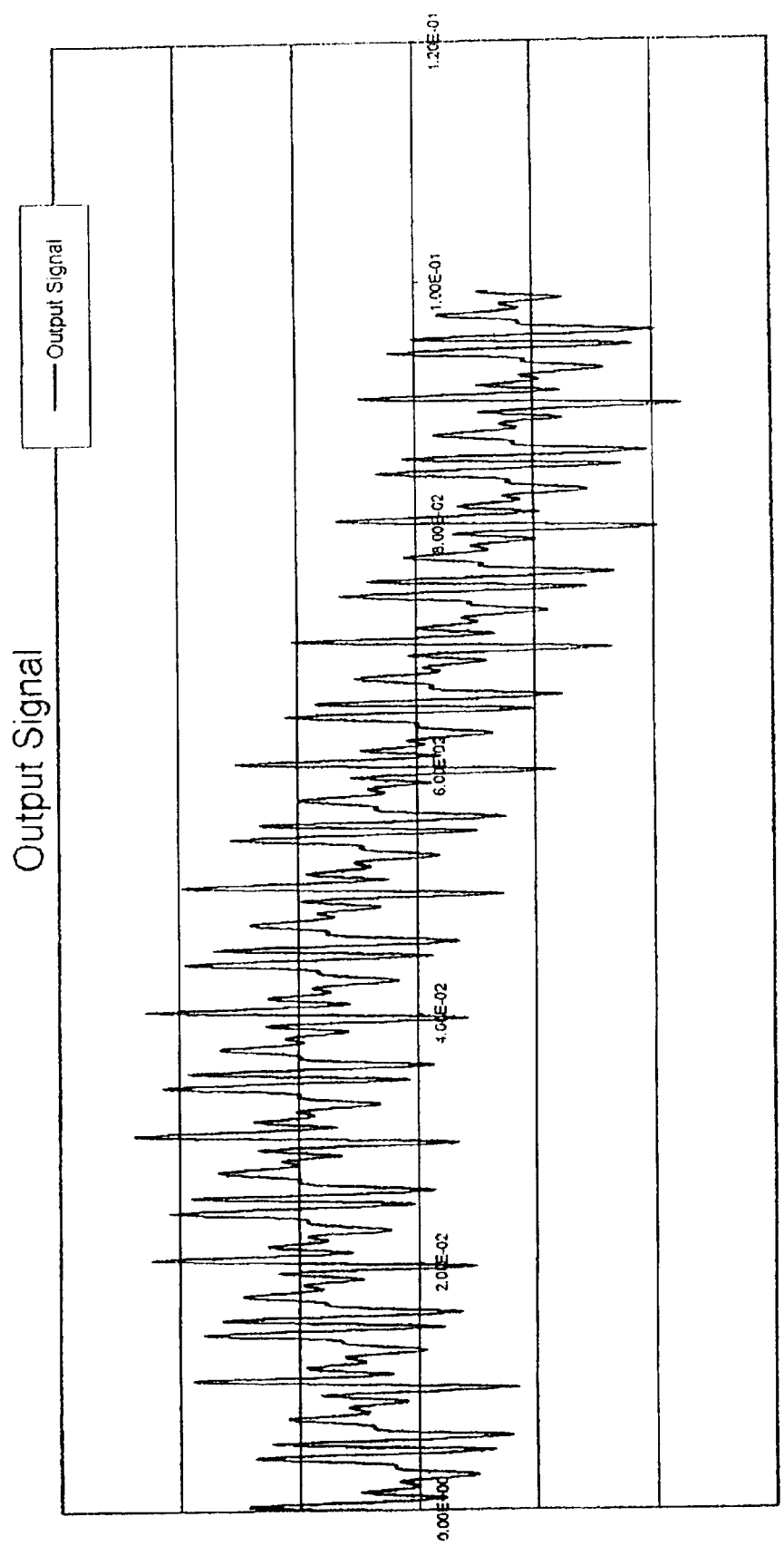
Figure 8C:
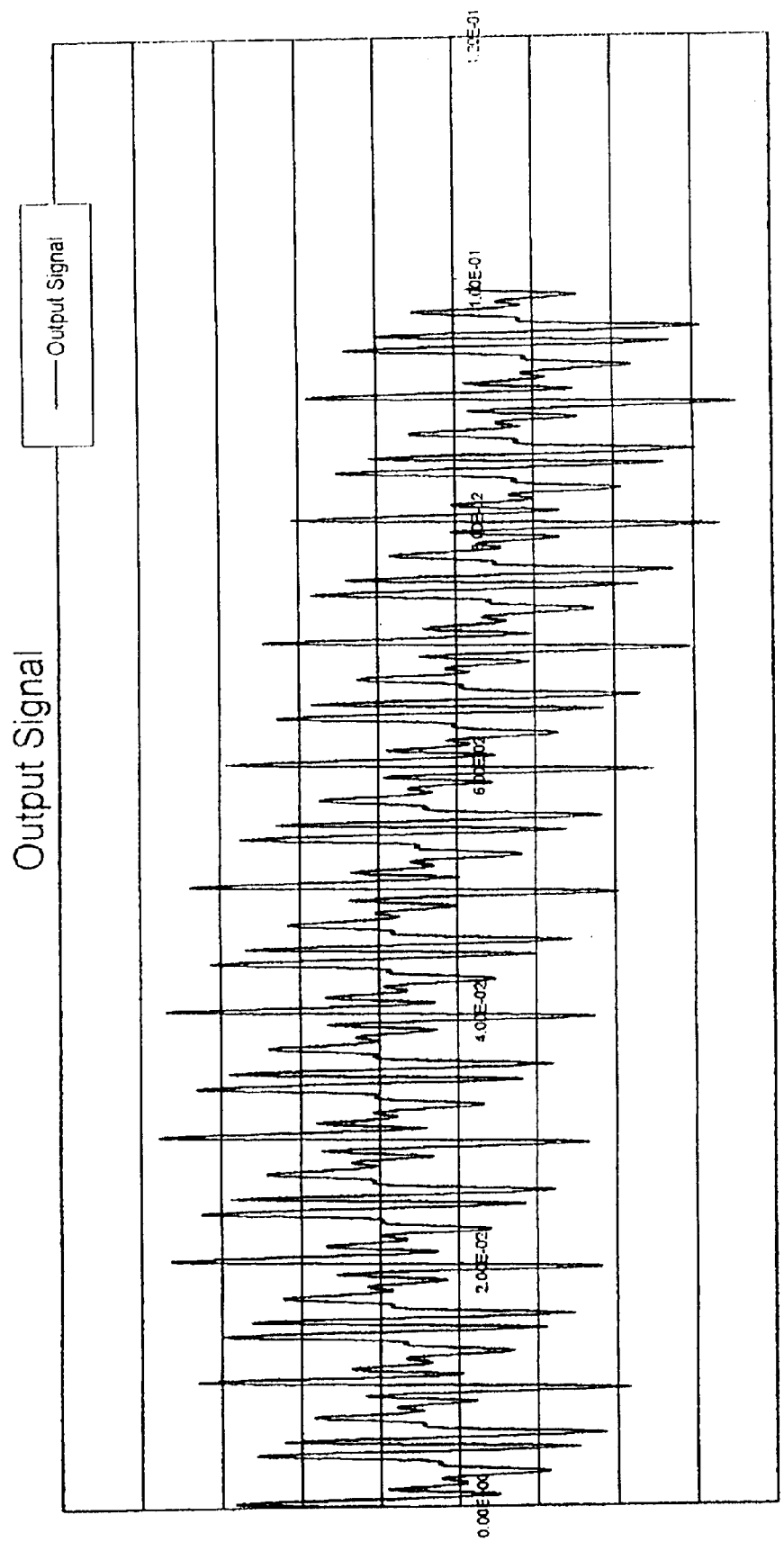

FIGS. 8A to 8C each show upper and lower graphs in a similar format to that of FIGS. 6A to 6C respectively, except that the frequency of the user signal is 8 Hz.

Figure 9A:
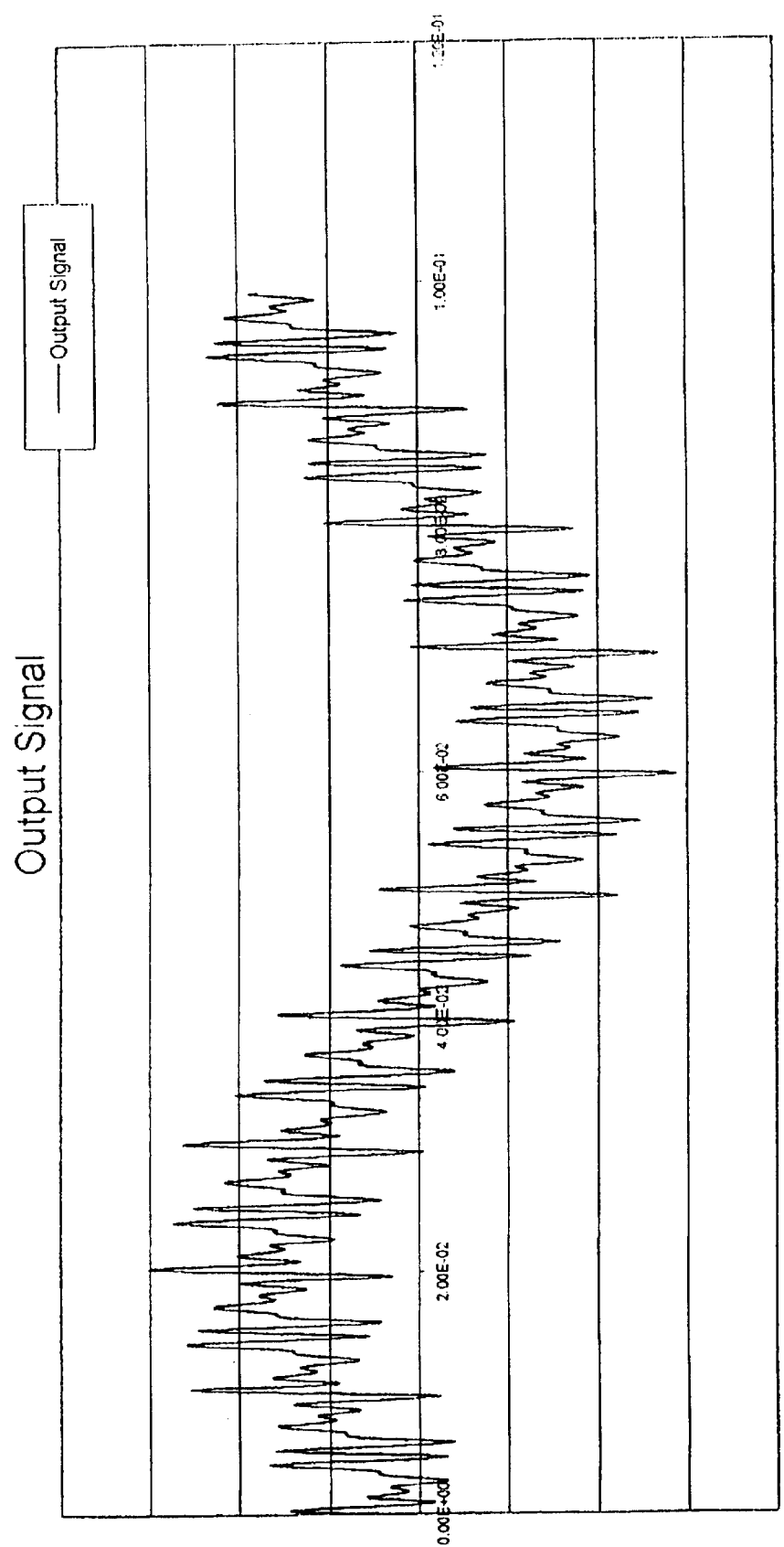
Figure 9B:
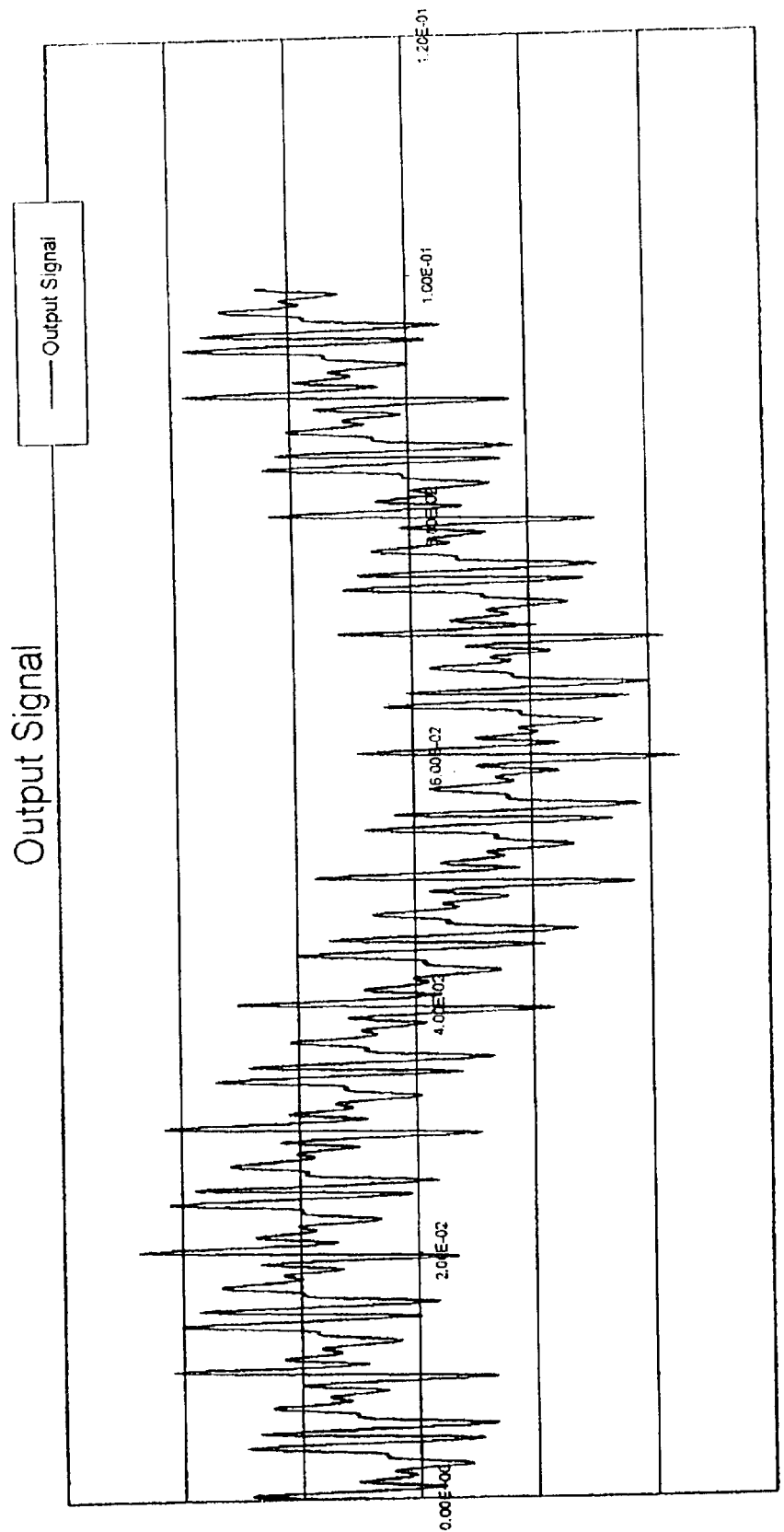
Figure 9C:
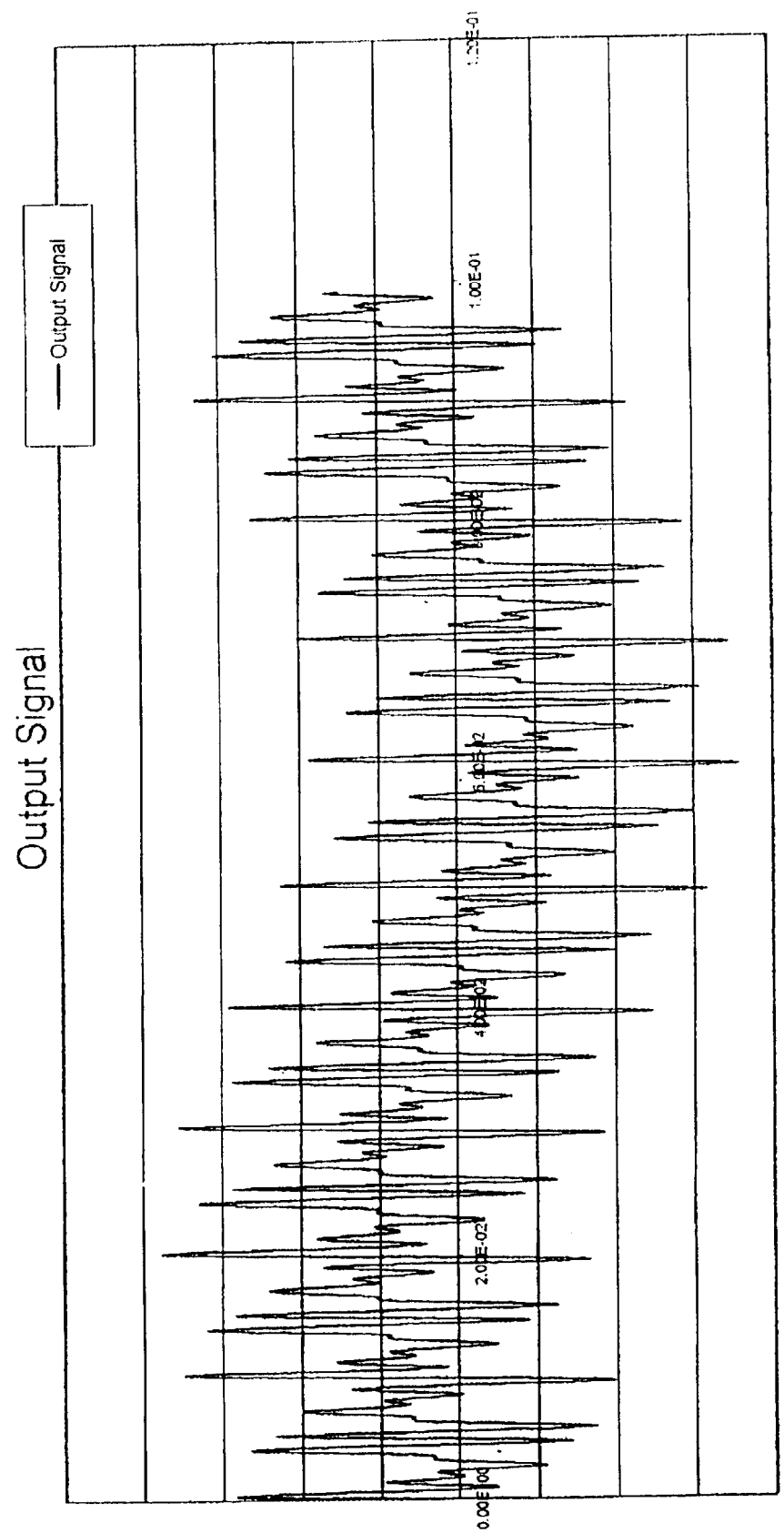

FIGS. 9A to 9C each show upper and lower graphs in a similar format to that of FIGS. 6A to 6C respectively, except that the frequency of the user signal is 12 Hz.

Figure 10A:
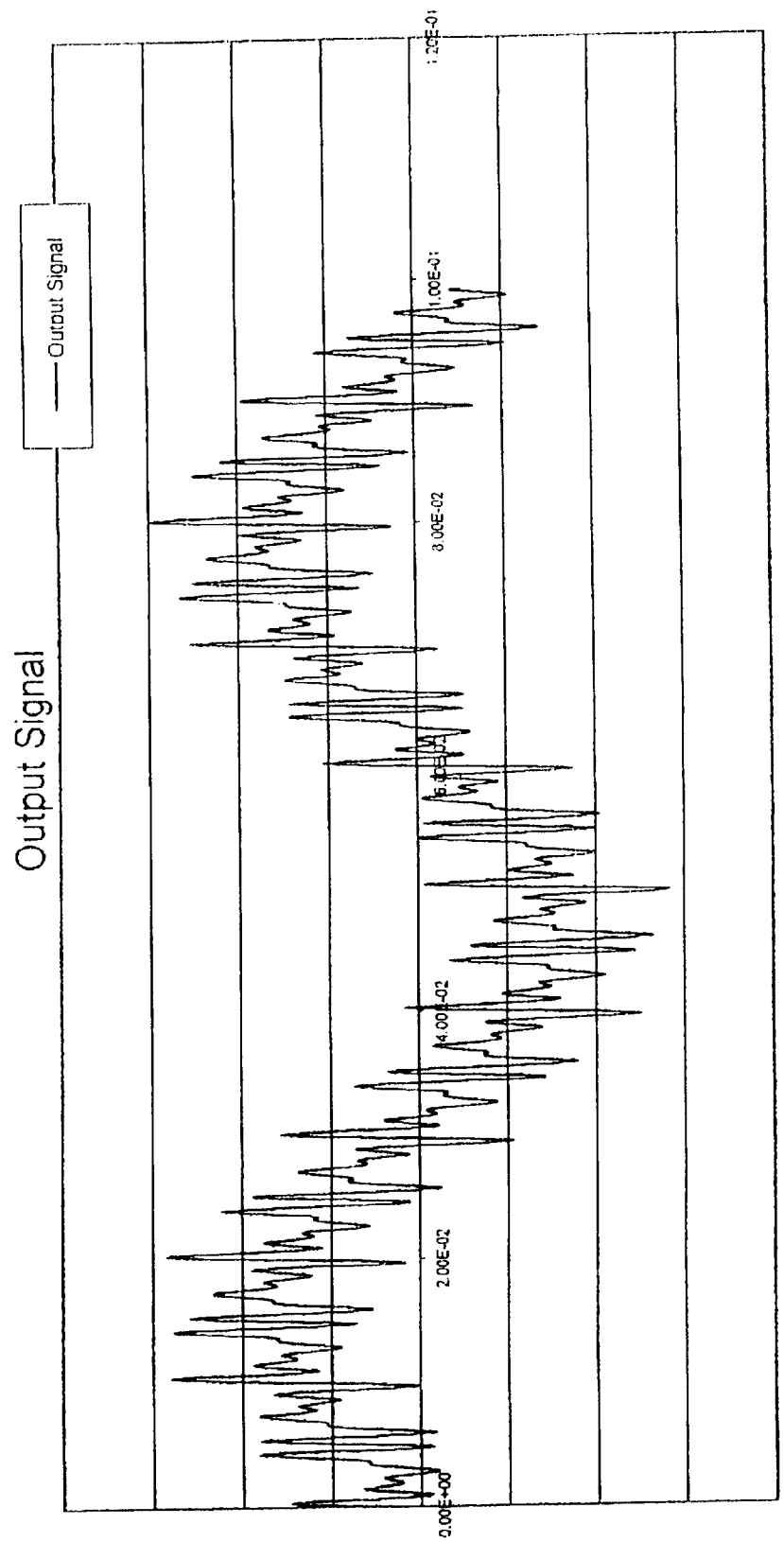
Figure 10B:
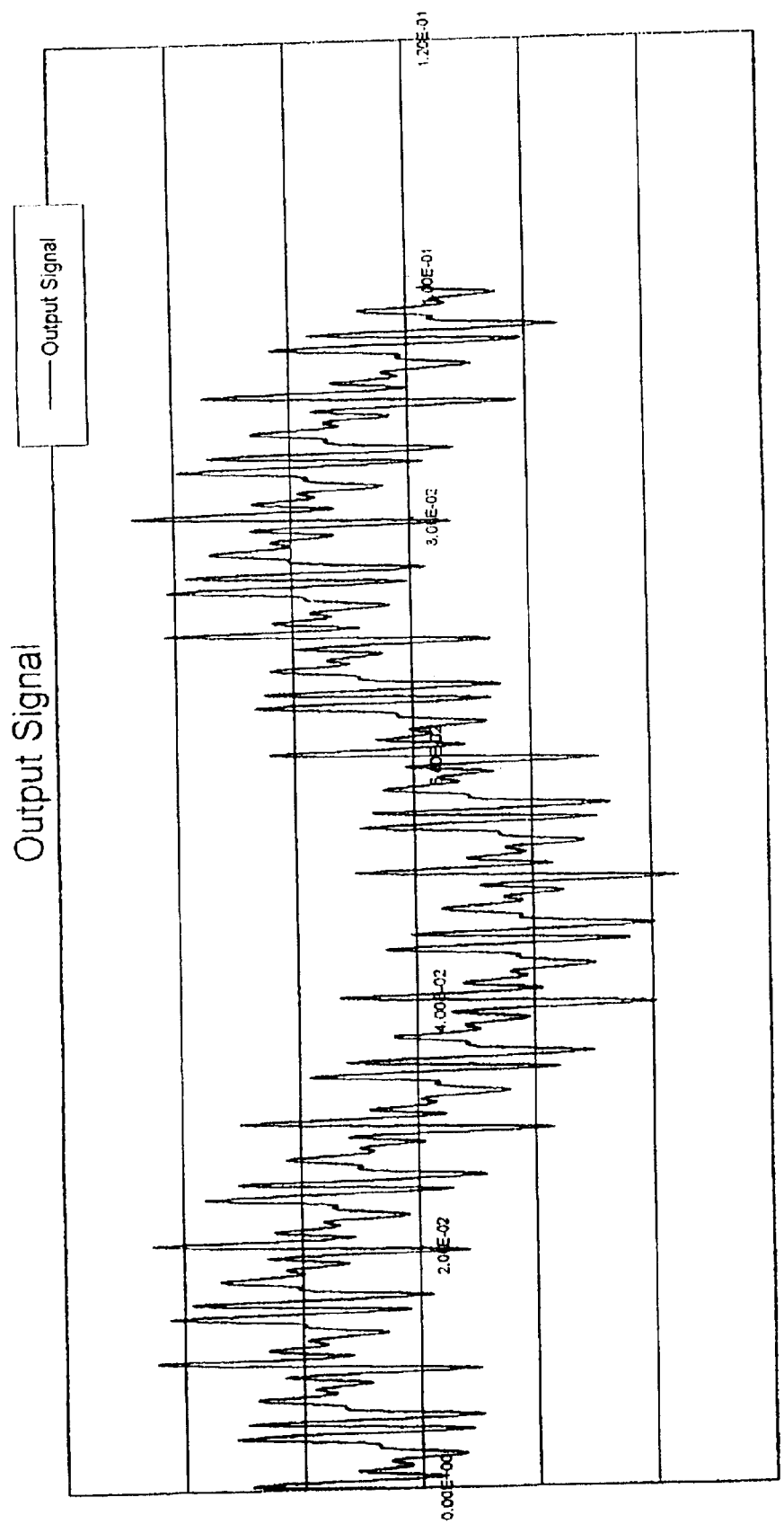
Figure 10C:
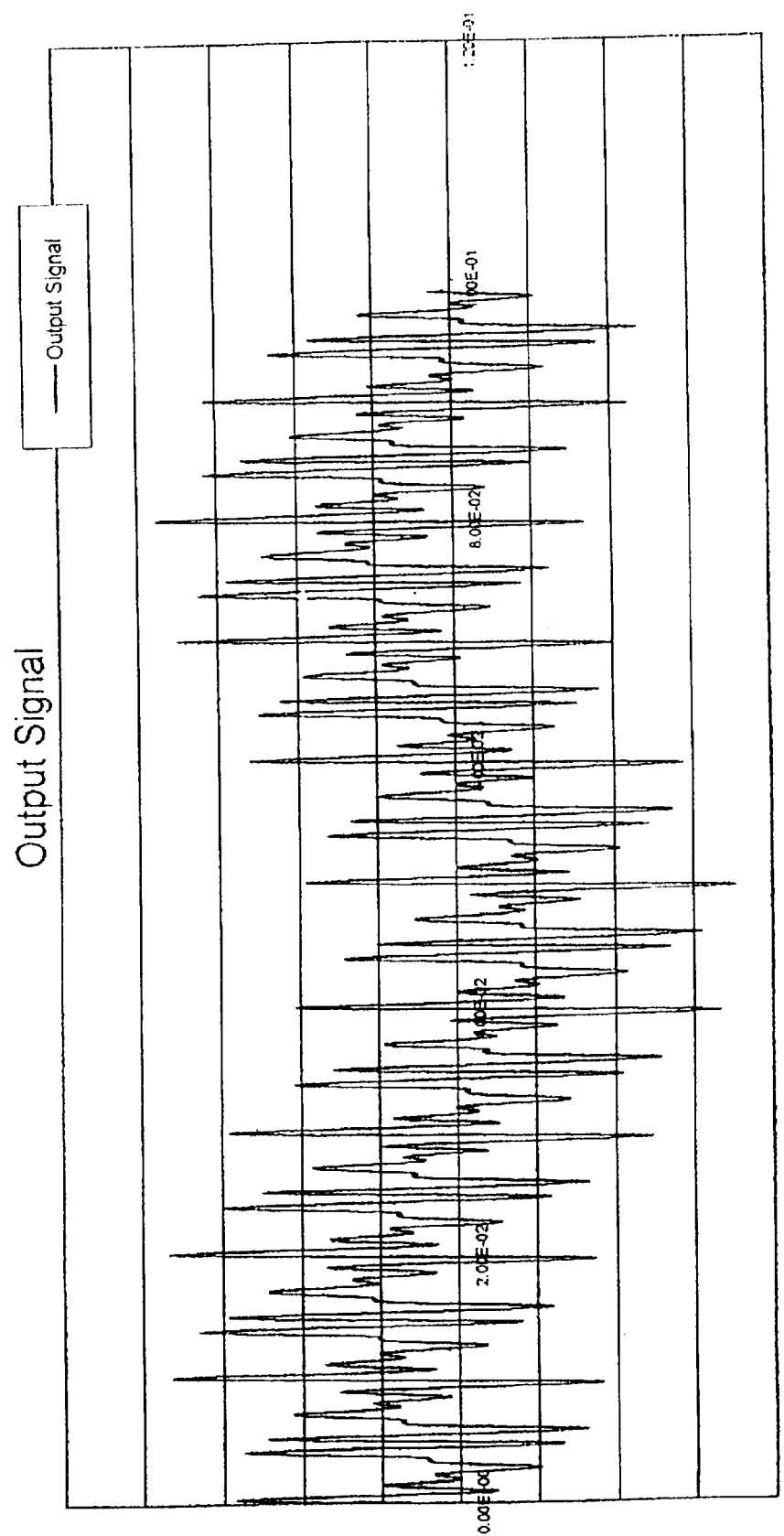

FIGS. 10A to 10C each show upper and lower graphs in a similar format to that of FIGS. 6A to 6C respectively, except that the frequency of the user signal is 16 Hz.

Figure 11A:
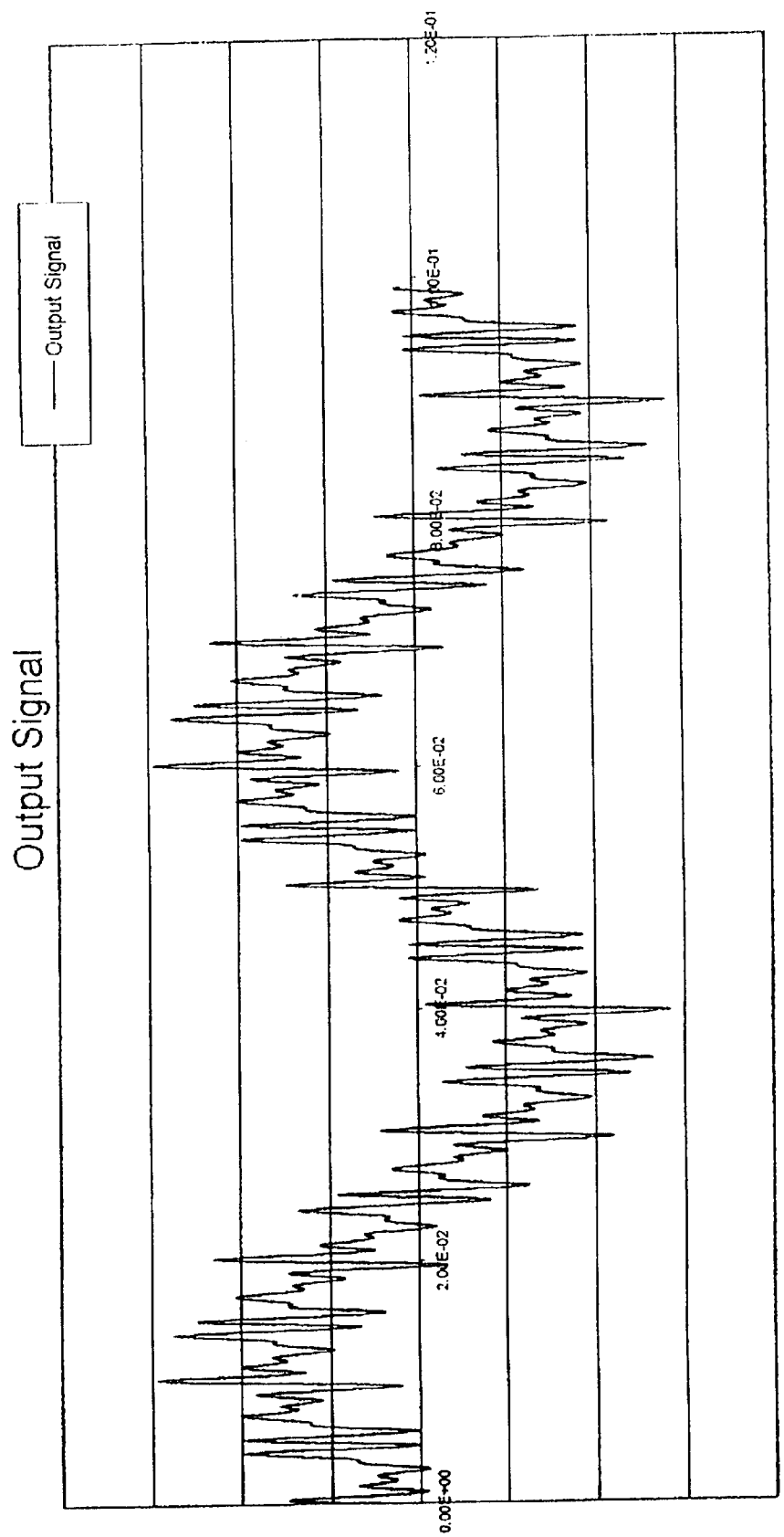
Figure 11B:
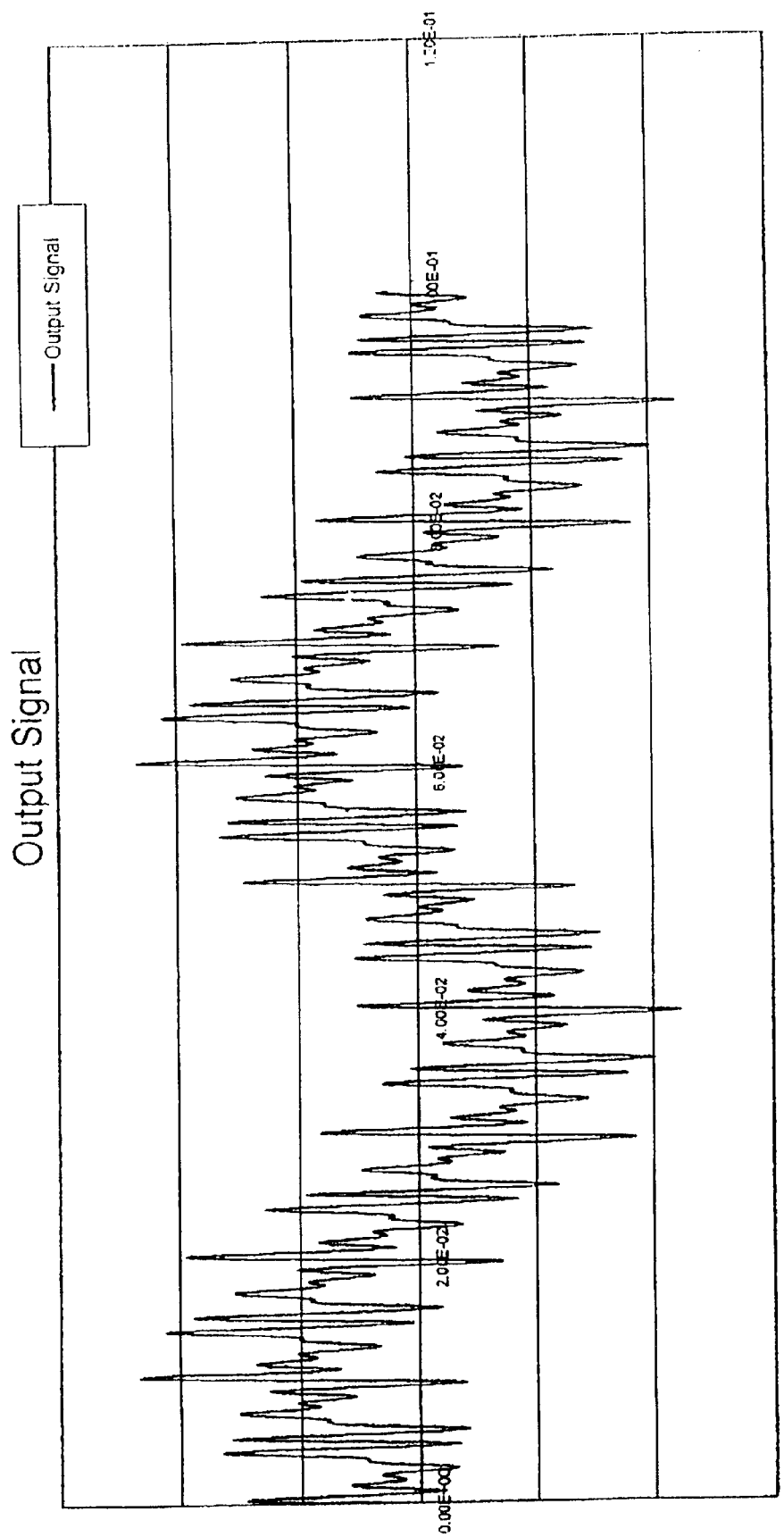
Figure 11C:
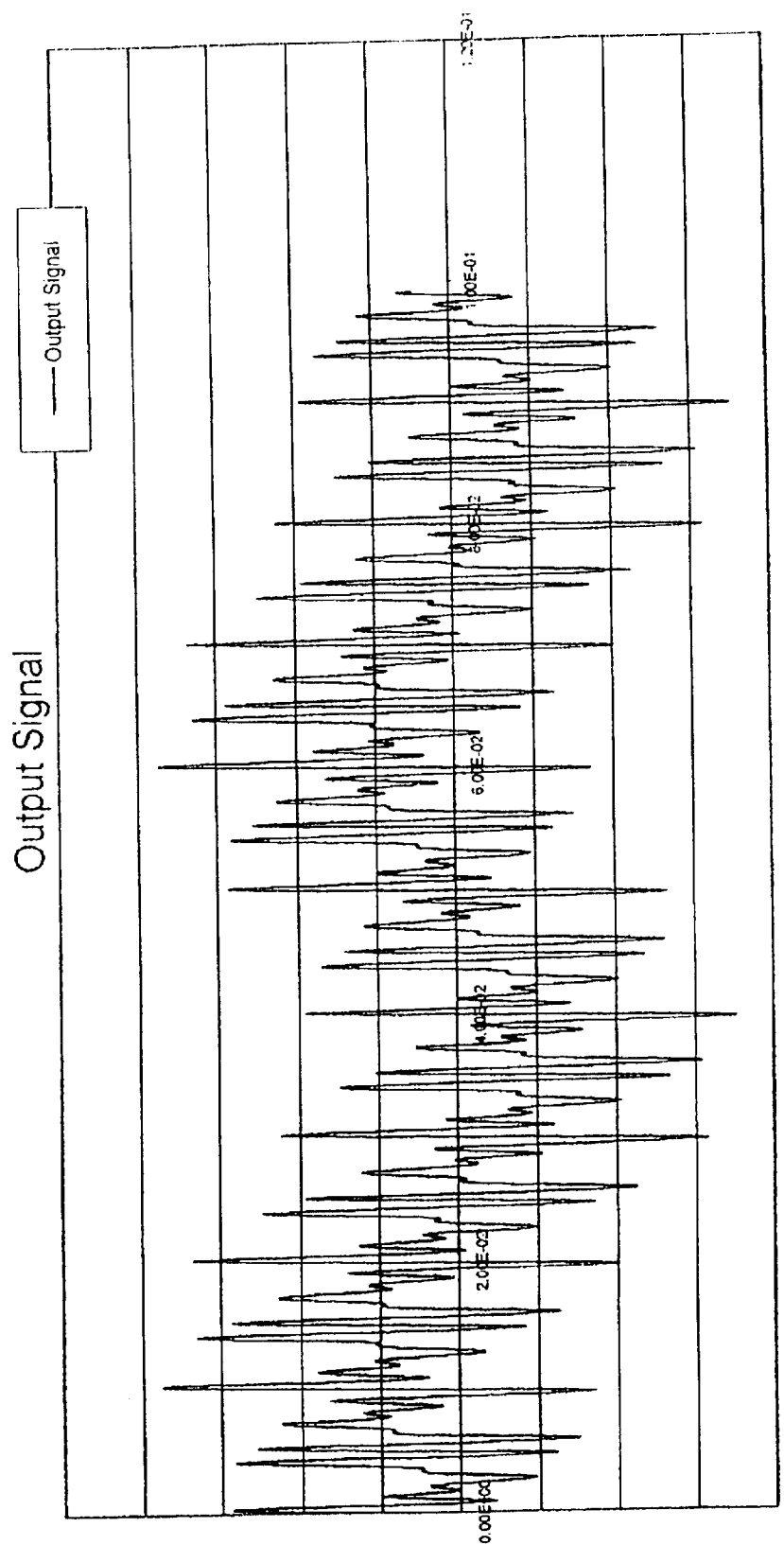

FIGS. 11A to 11C each show upper and lower graphs in a similar format to that of FIGS. 6A to 6C respectively, except that the frequency of the user signal is 20 Hz.

Figure 12A:
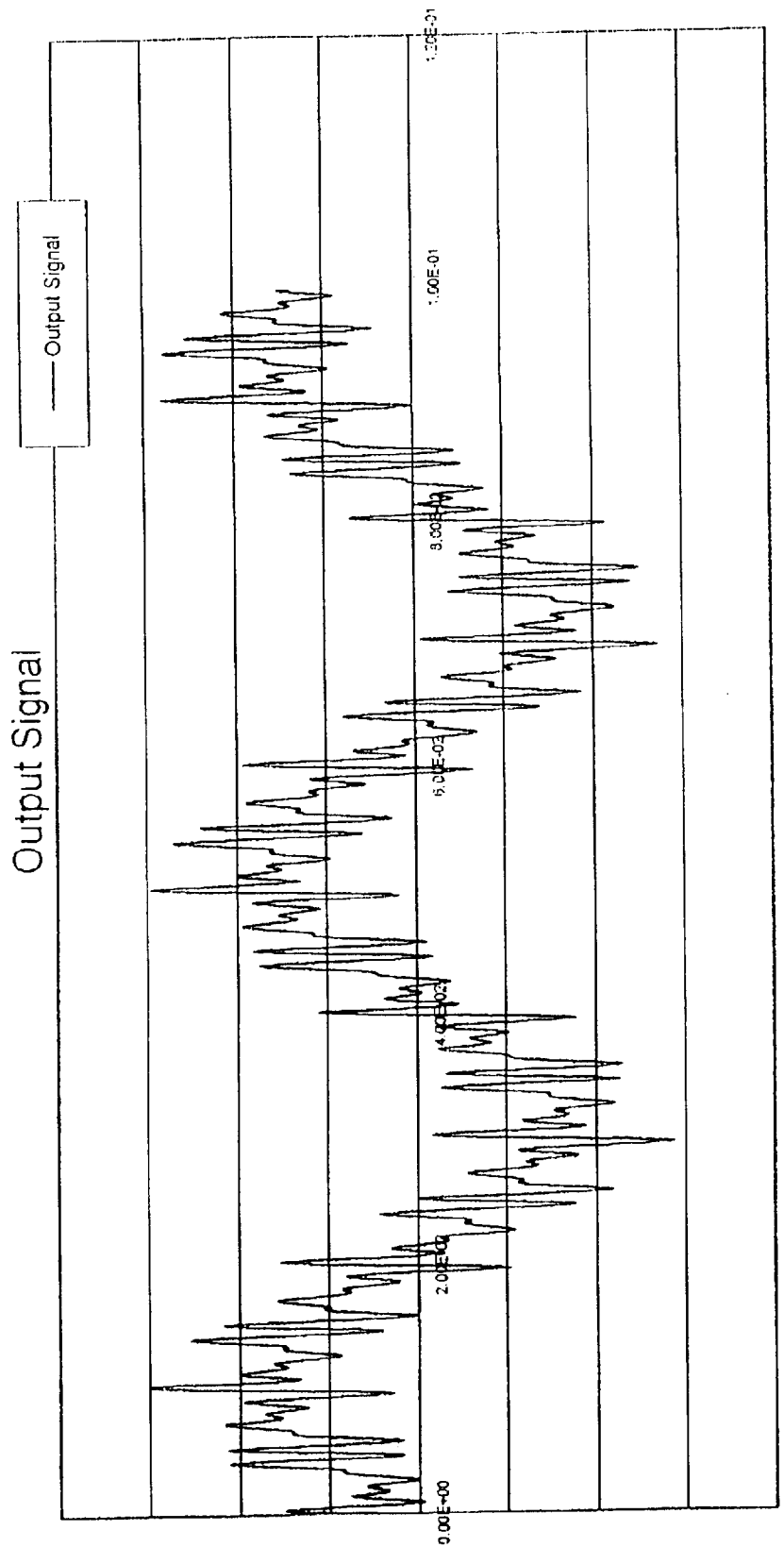
Figure 12B:
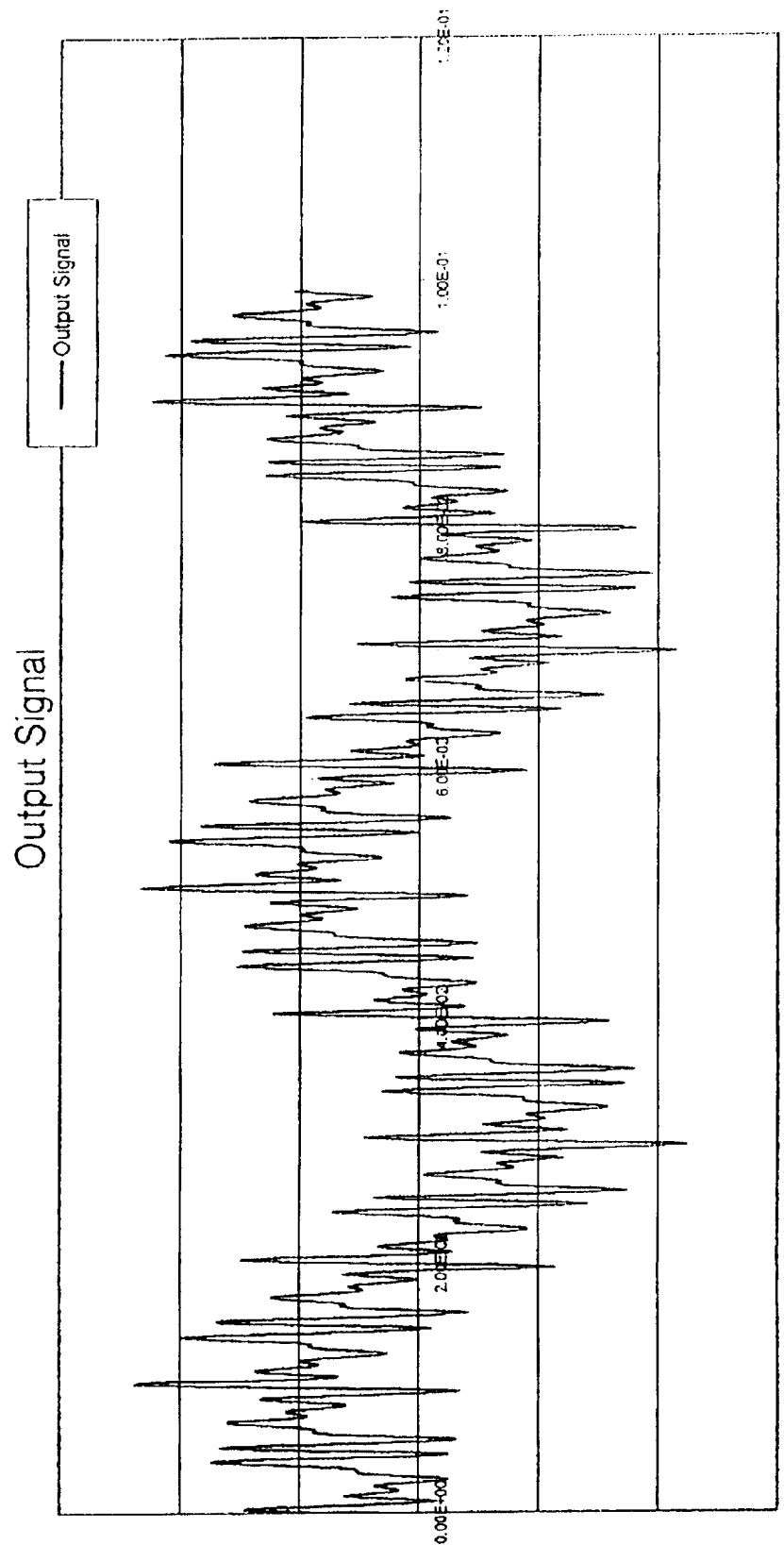
Figure 12C:
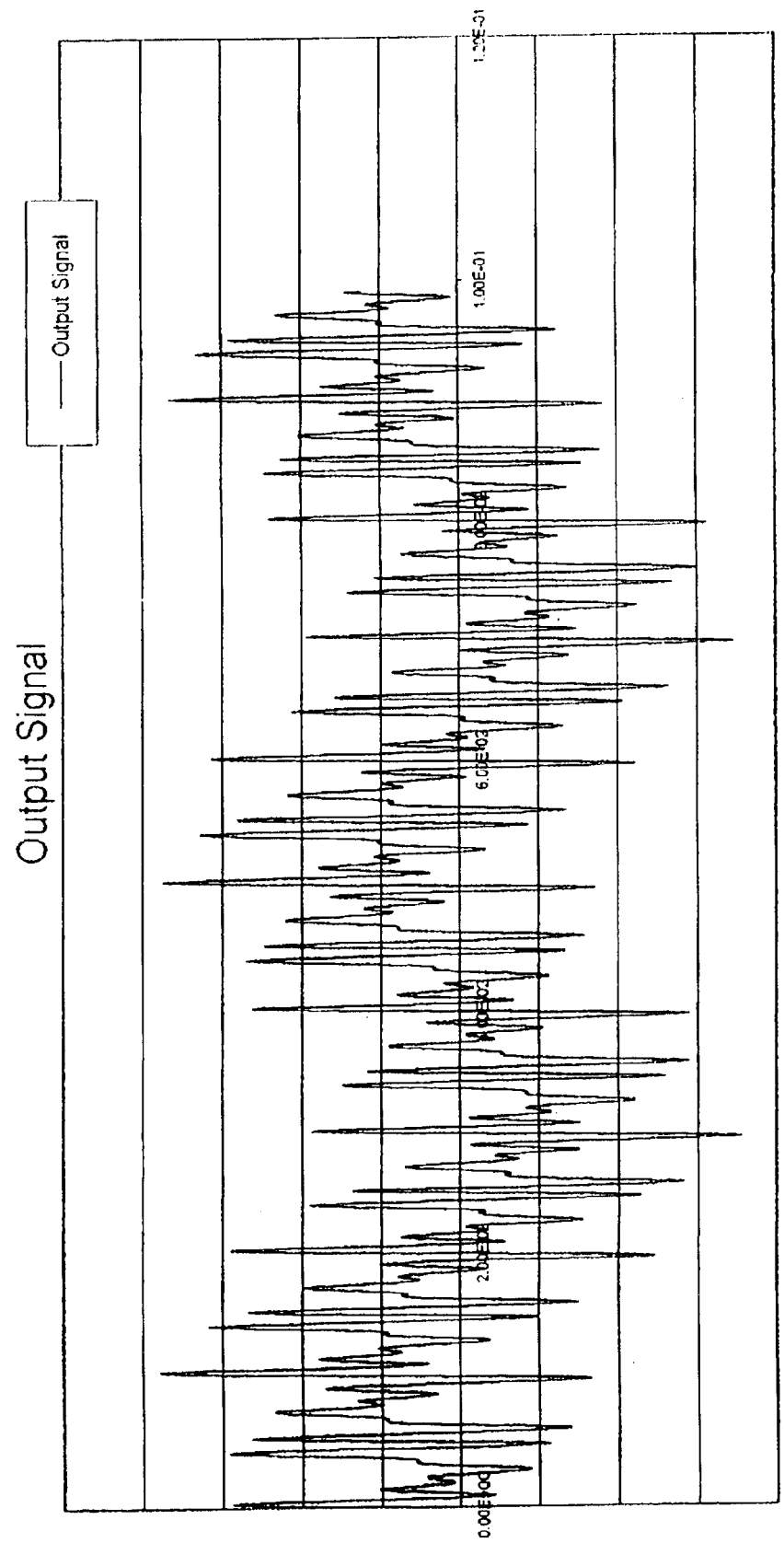

FIGS. 12A to 12C each show upper and lower graphs in a similar format to that of FIGS. 6A to 6C respectively, except that the frequency of the user signal is 24 Hz.

Figure 13A:
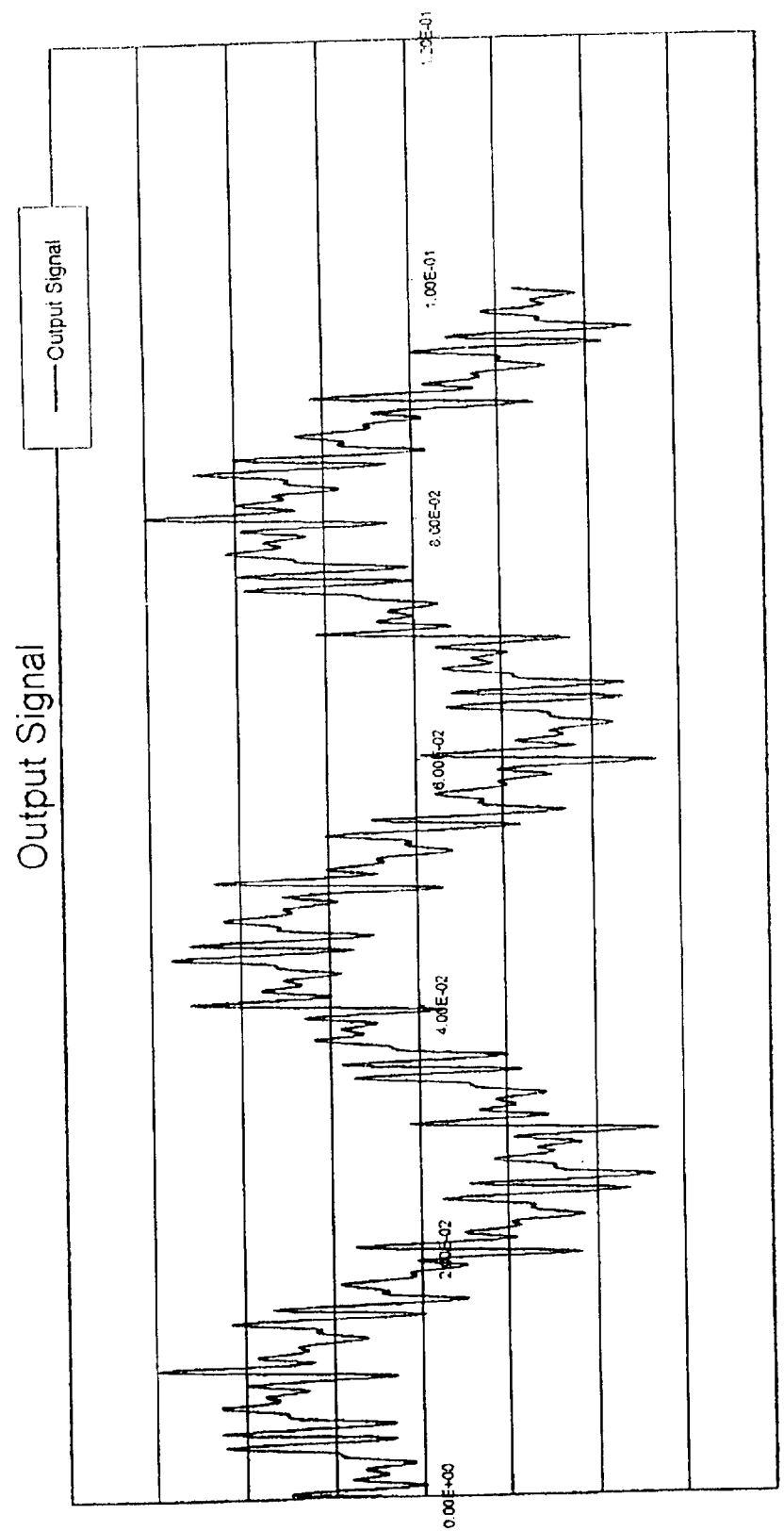
Figure 13B:
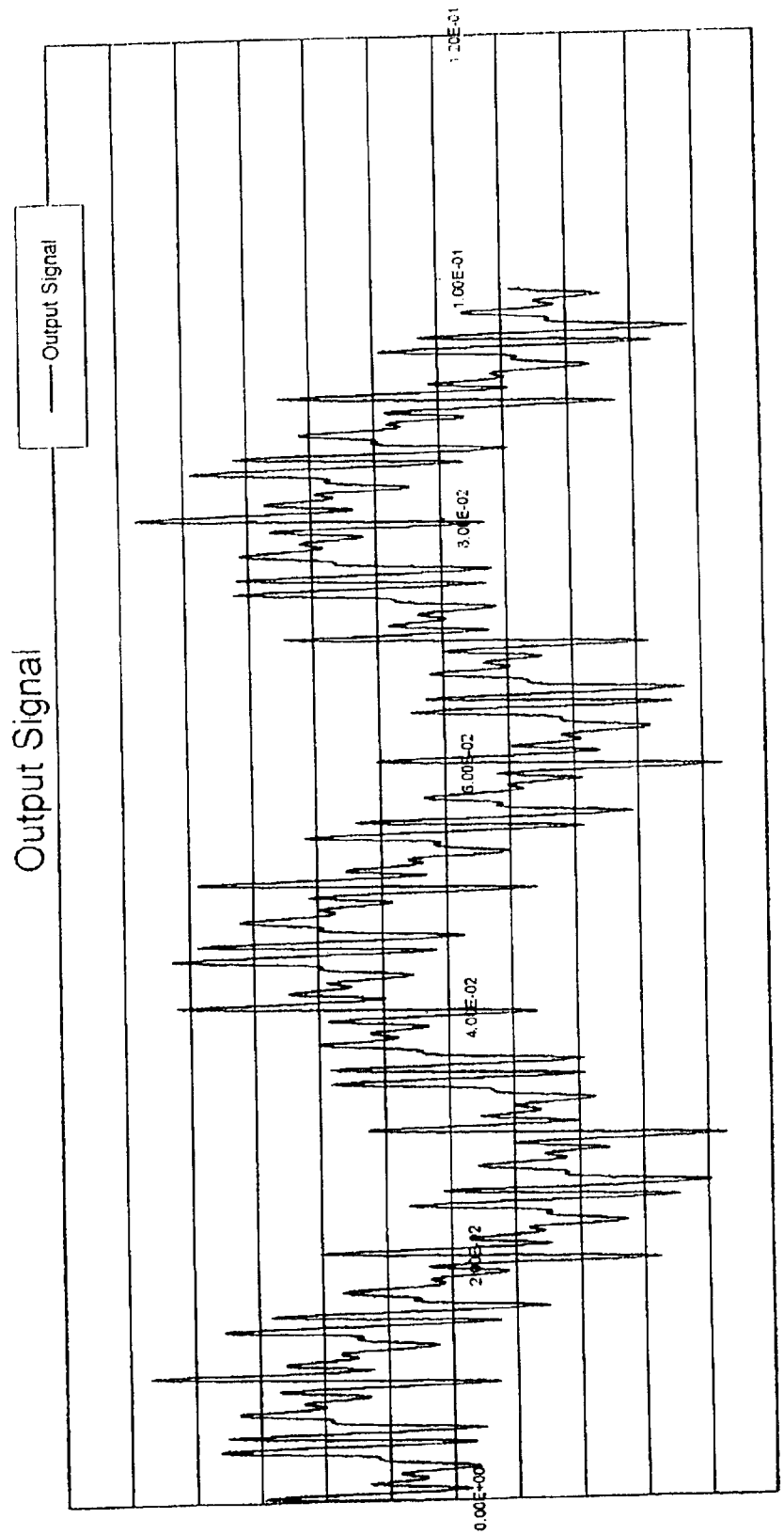
Figure 13C:
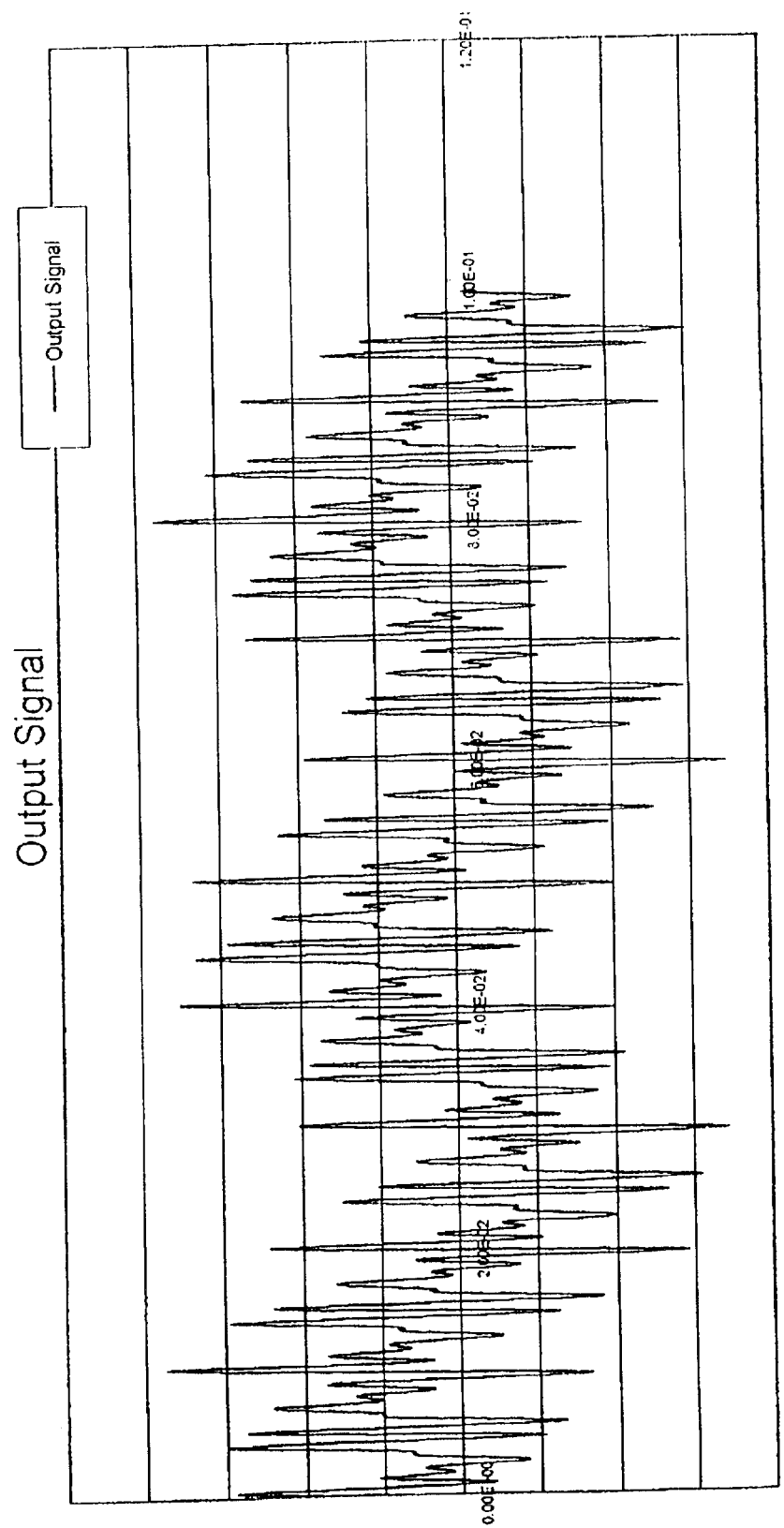

FIGS. 13A to 13C each show upper and lower graphs in a similar format to that of FIGS. 6A to 6C respectively, except that the frequency of the user signal is 28 Hz.

Figure 14A:
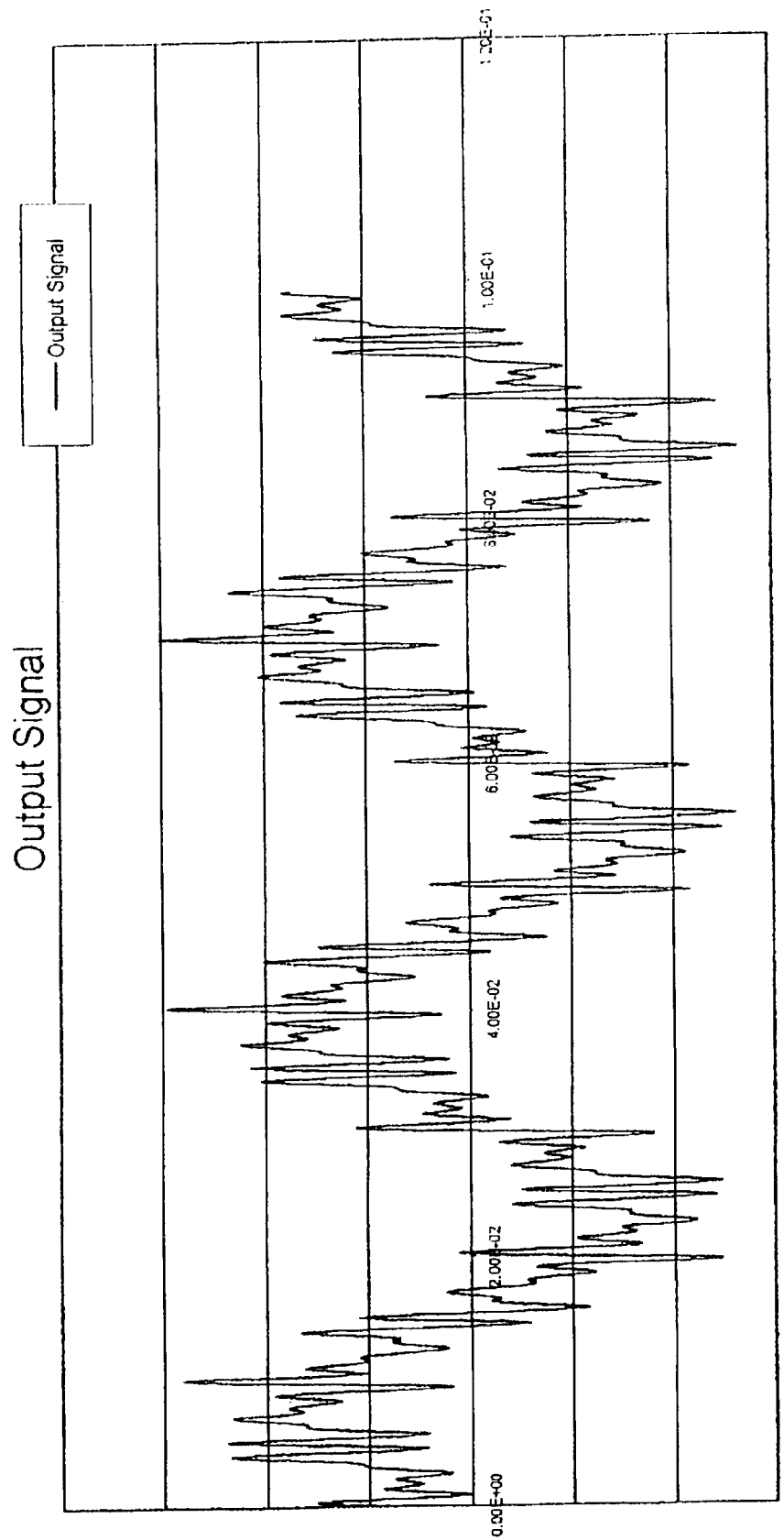
Figure 14B:
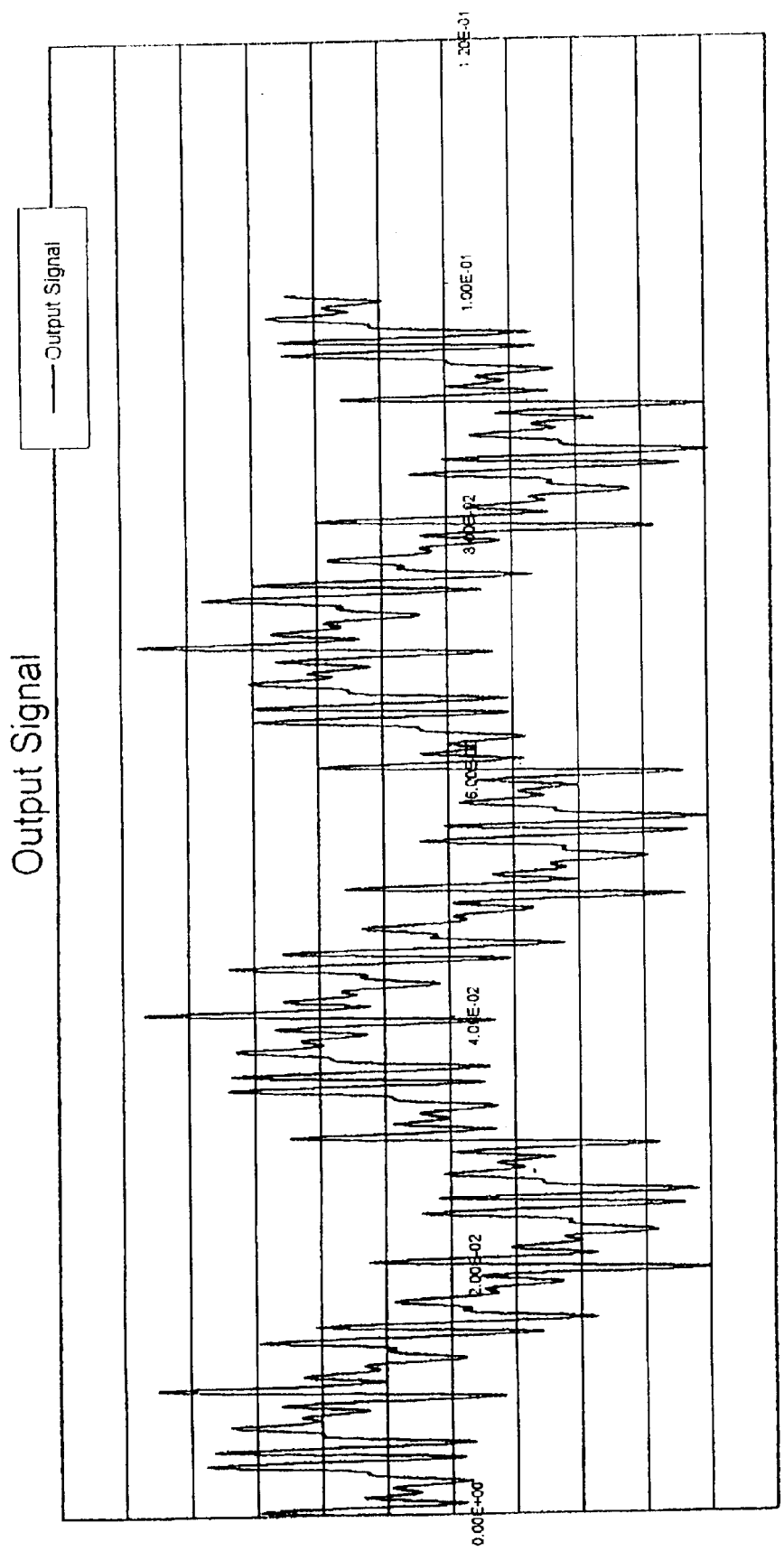
Figure 14C:
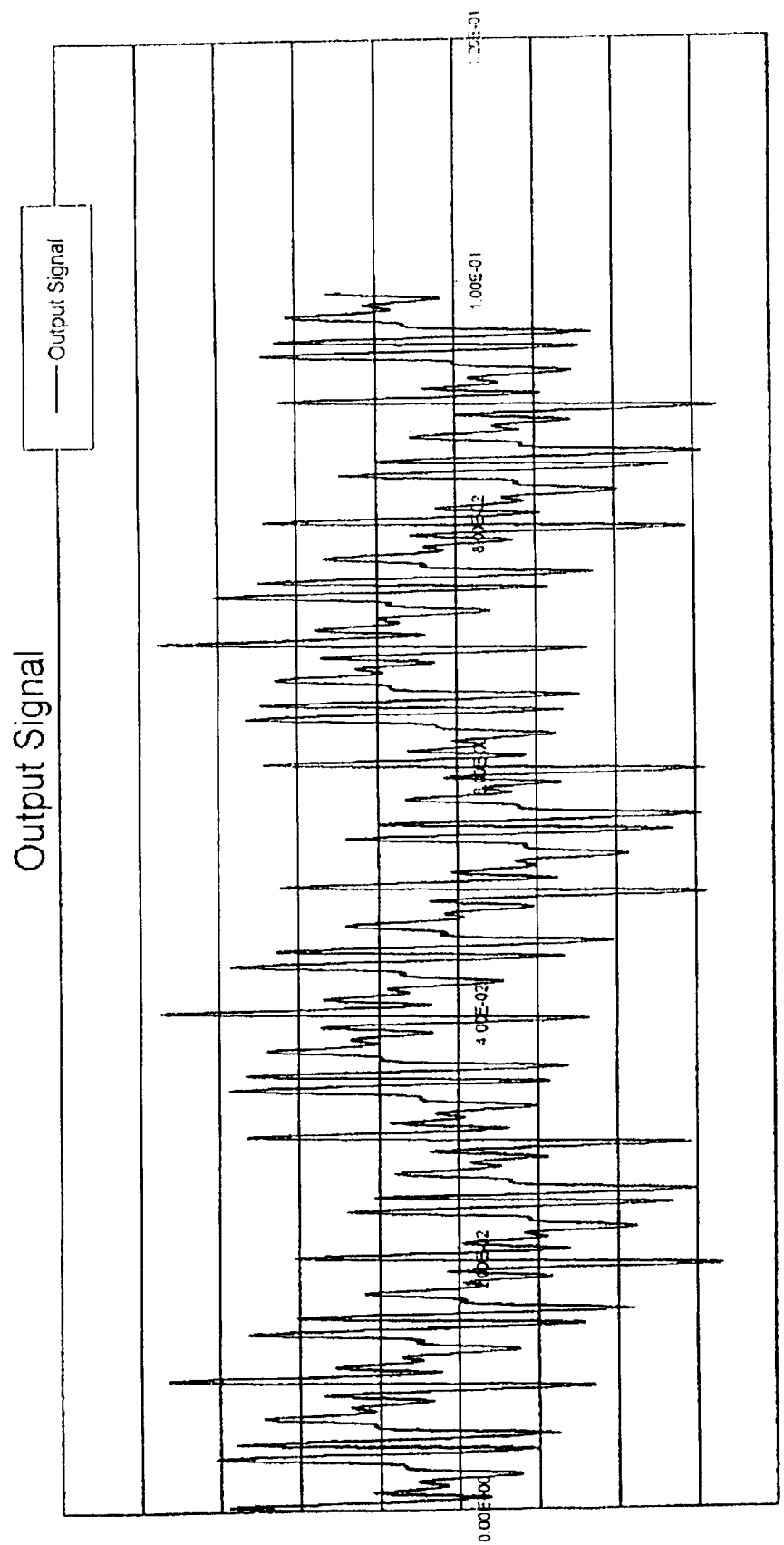
Figure 15A:
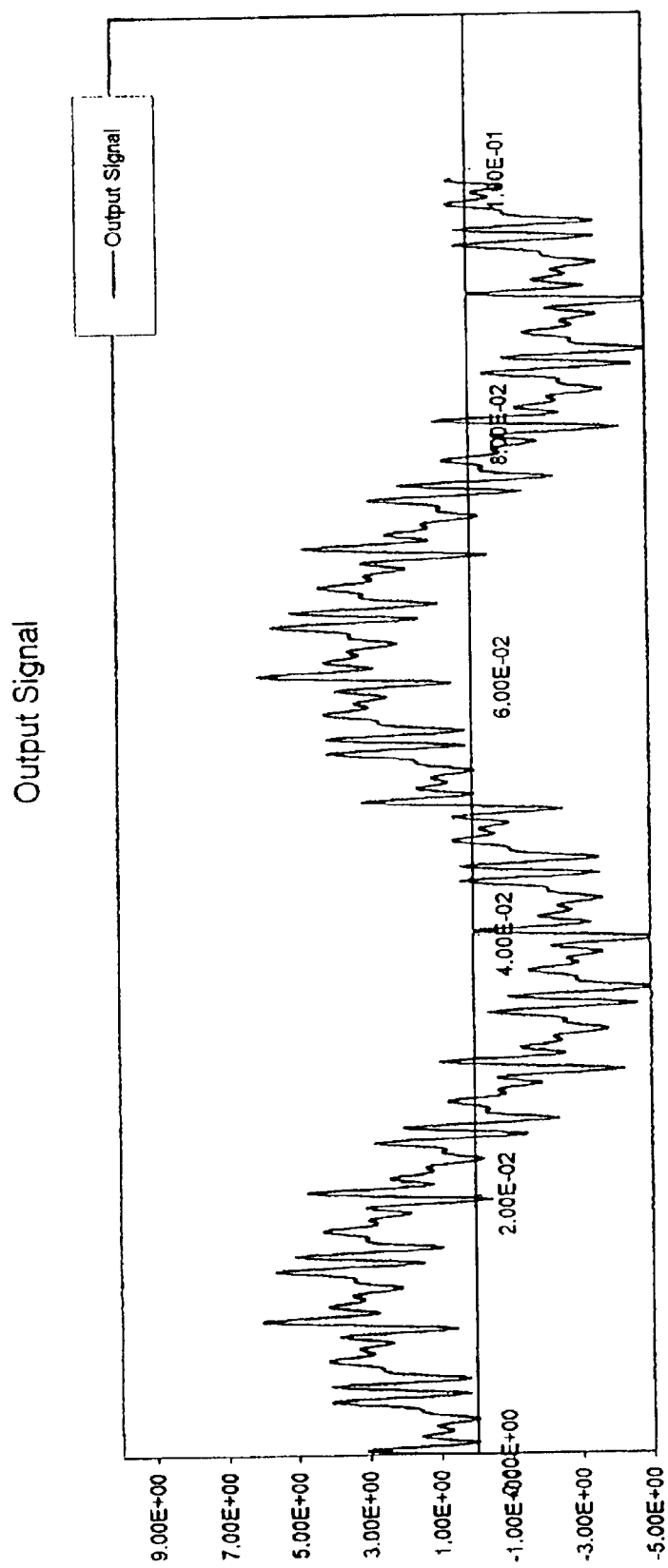
FIGS. 15A to 15B each illustrate a time domain representations similar to that of FIG. 6A, although using modified parameters as will be described.
Figure 15B:
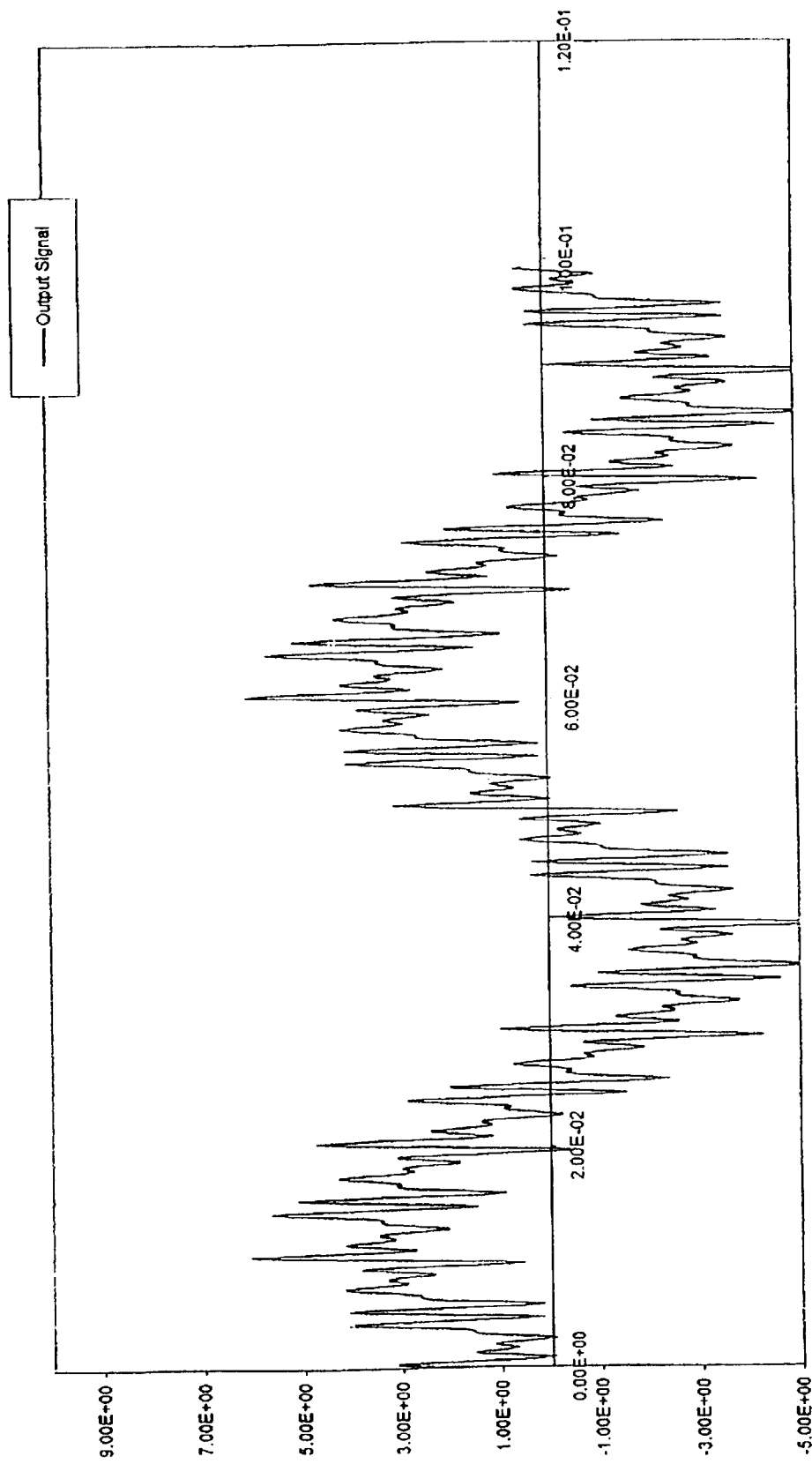

FIGS. 14A to 14C each show upper and lower graphs in a similar format to that of FIGS. 6A to 6C respectively, except that the frequency of the user signal is 32 Hz.

An example of a system that could be provided for a user or patient operable apparatus includes the selective availability from a group of the six "main" programs ("MP-1" to "MP-5"), and two "short" programs ("SP-1" and SP-2"). These programs vary in their frequency patterns and amplitude factors, and are as follows.

Operation of Therapeutic Programs

During operation of all of the following programs, the user interface panel 10 displays the intensity of the coil/s in terms of six increments over the full range of available intensities for that particular program.

Main Program no. 1—Vitalisation/Blood Circulation: The total duration is 15 minutes by default, although the user can adjust this up to a maximum of 30 minutes. The intensity is 1.5 $\mu$T by default, although the user can adjust this value up to a maximum of 1.5 $\mu$T.

| User Signal Frequency $\mu_M(t)$ (Hz) | Duration (sec) | Amplitude Factor (%) |
|---|---|---|
| 21 | 20 | 30 |
| 18 | 20 | 40 |
| 16 | 20 | 50 |
| 15 | 30 | 60 |
| 14 | 60 | 80 |
| 13 | 120 | 100 |
| 12 | 140 | 100 |
| 11 | 140 | 100 |
| 10 | 140 | 100 |
| 9 | 120 | 100 |
| 8 | 60 | 80 |
| 8 | 30 | 50 |
| TOTAL | 900 secs or 15 mins. | |

Main Program no. 2—Relaxation: The total duration is 15 minutes by default, although the user can adjust this between a minimum of 5 minutes and a maximum of 30 minutes. The intensity is 1.5 $\mu$T by default, although the user can adjust this value to a maximum of 15 $\mu$T.

| User Signal Frequency $\mu_M(t)$ (Hz) | Duration (sec) | Amplitude Factor (%) |
|---|---|---|
| 17 | 10 | 20 |
| 16 | 10 | 25 |
| 15 | 10 | 25 |
| 14 | 10 | 30 |
| 13 | 10 | 30 |
| 12 | 10 | 40 |
| 11 | 20 | 50 |
| 10 | 20 | 60 |
| 9 | 20 | 70 |
| 8 | 20 | 80 |
| 7 | 60 | 100 |
| 6 | 80 | 100 |
| 5 | 140 | 100 |
| 4 | 240 | 100 |
| 3 | 180 | 100 |
| 3 | 20 | 80 |
| 3 | 15 | 60 |
| 3 | 15 | 30 |
| 3 | 10 | 0 |
| TOTAL | 900 secs or 15 mins. | |

Main Program no. 3—Vigilance/Activation: The total duration is 15 minutes by default, although the user can adjust this from a minimum of 5 minutes and to a maximum of 30 minutes. The intensity is 1.5 $\mu$T by default, although the user can adjust this to a maximum of 15 $\mu$T.

| User Signal Frequency $\mu_M(t)$ (Hz) | Duration (sec) | Amplitude Factor (%) |
|---|---|---|
| 5 | 10 | 50 |
| 6 | 20 | 70 |
| 7 | 20 | 90 |
| 8 | 60 | 100 |
| 9 | 80 | 100 |
| 10 | 150 | 100 |
| 11 | 150 | 100 |
| 12 | 120 | 100 |
| 13 | 60 | 80 |
| 14 | 60 | 70 |
| 15 | 60 | 60 |
| 16 | 30 | 50 |
| 17 | 30 | 40 |
| 18 | 30 | 30 |
| 21 | 20 | 20 |
| TOTAL | 900 secs or 15 mins. | |

Main Program no. 4—Pain: The total duration is 15 minutes by default, although the user can adjust this to a maximum of 30 minutes. The intensity is 1.5 $\mu$T by default, although the user can adjust this to a maximum of 150 $\mu$T. It is noted that the user interface panel 10 will still display increments from step 1 to step 6, so as to maintain compatibility with the other programs which have a maximum of 15 $\mu$T at full scale.

| User Signal Frequency $\mu_M(t)$ (Hz) | Duration (sec) | Amplitude Factor (%) |
|---|---|---|
| 32 | 30 | 50 |
| 30 | 30 | 80 |
| 28 | 40 | 100 |
| 26 | 80 | 100 |

-continued

| User Signal Frequency $\mu_M(t)$ (Hz) | Duration (sec) | Amplitude Factor (%) |
|---|---|---|
| 24 | 120 | 100 |
| 22 | 120 | 100 |
| 20 | 80 | 100 |
| 16 | 60 | 80 |
| 14 | 40 | 50 |
| 12 | 20 | 20 |
| 10 | 20 | 20 |
| 8 | 20 | 20 |
| 7 | 100 | 100 |
| 6 | 120 | 100 |
| 6 | 20 | 50 |
| TOTAL | 900 secs or 15 mins. | |

Main Program no. 5: Relaxation and Revitalisation: The total duration is 30 minutes by default. This program provides 1.5 $\mu$T by default, although is adjustable by the user up to a maximum of 15 $\mu$T.

| User Signal Frequency $\mu_M(t)$ (Hz) | Duration (sec) | Amplitude Factor (%) |
|---|---|---|
| 17 | 10 | 20 |
| 16 | 10 | 25 |
| 15 | 10 | 25 |
| 14 | 10 | 30 |
| 13 | 10 | 30 |
| 12 | 10 | 40 |
| 11 | 20 | 50 |
| 10 | 20 | 60 |
| 9 | 20 | 70 |
| 8 | 20 | 80 |
| 7 | 60 | 100 |
| 6 | 80 | 100 |
| 5 | 140 | 100 |
| 4 | 240 | 100 |
| 3 | 180 | 100 |
| 3 | 20 | 80 |
| 3 | 15 | 60 |
| 3 | 15 | 30 |
| 3 | 10 | 0 |
| 5 | 10 | 50 |
| 6 | 20 | 70 |
| 7 | 20 | 90 |
| 8 | 60 | 100 |
| 9 | 80 | 100 |
| 10 | 150 | 100 |
| 11 | 150 | 100 |
| 12 | 120 | 100 |
| 13 | 60 | 80 |
| 14 | 60 | 70 |
| 15 | 60 | 60 |
| 16 | 30 | 50 |
| 17 | 30 | 40 |
| 18 | 30 | 30 |
| 21 | 20 | 20 |
| TOTAL | 30 mins. | |

Figure 16:
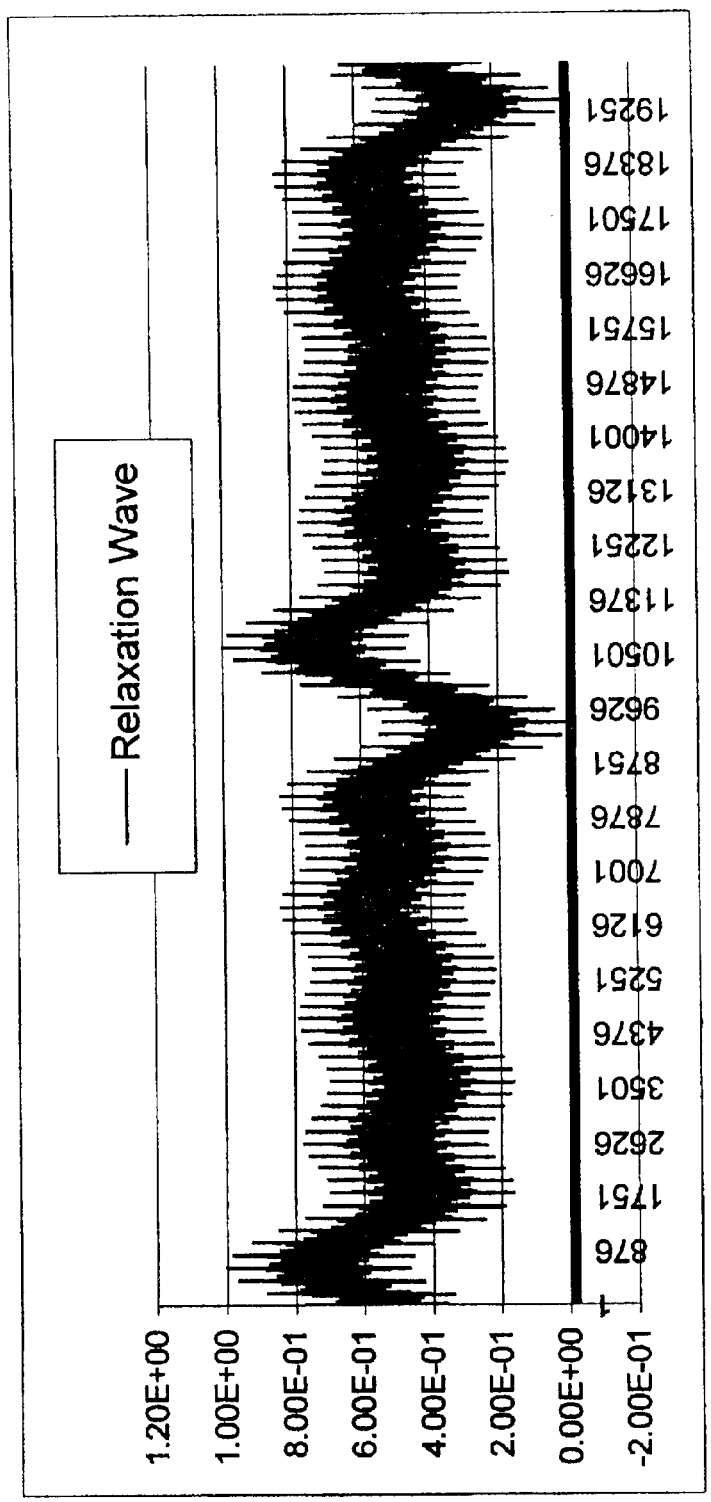
FIG. 16 shows a time domain waveform for operation intended to promote sleep.

Main Program no. 6: Sleep: For this program a variable time can be chosen, with the basic signal at 80% together wit the superposition of each of a 2 Hz, 3 Hz, 4 Hz and 5 Hz signals. This is shown in FIG. 16. The inventor believes the characteristic 'wobble' that is evident in the composite waveform is responsible for assisting in advancing sleep. The amplitude of the basic signal reduces from 80% to 40% linearly over the course of the program. For example, if 40 minutes is chosen, then the amplitude reduces at 1% per minute.

Short Program no. 1—Vitality/Blood Circulation: The total duration is 5 minutes by default, although the user can adjust this to a maximum of 30 minutes. The intensity is 1.5 $\mu$T by default, although the user can adjust this to a maximum of 15 $\mu$T.

| User Signal Frequency $\mu_M(t)$ (Hz) | Duration (sec) | Amplitude Factor (%) |
|---|---|---|
| 21 | 7 | 30 |
| 18 | 7 | 40 |
| 16 | 7 | 50 |
| 15 | 11 | 60 |
| 14 | 20 | 80 |
| 13 | 40 | 100 |
| 12 | 46 | 100 |
| 11 | 46 | 100 |
| 10 | 46 | 100 |
| 9 | 40 | 100 |
| 8 | 20 | 80 |
| 8 | 10 | 50 |
| TOTAL | 5 mins. | |

Short Program no. 2—Vigilance/Activation: The total duration is 5 minutes by default, although the user can adjust this to a maximum of 30 minutes. The intensity is 1.5 $\mu$T by default, although the user can adjust this to a maximum of 15 $\mu$T.

| User Signal Frequency $\mu_M(t)$ (Hz) | Duration (sec) | Amplitude Factor (%) |
|---|---|---|
| 5 | 3 | 50 |
| 6 | 7 | 70 |
| 7 | 7 | 90 |
| 8 | 20 | 100 |
| 9 | 26 | 100 |
| 10 | 50 | 100 |
| 11 | 50 | 100 |
| 12 | 40 | 100 |
| 13 | 20 | 80 |
| 14 | 20 | 70 |
| 15 | 20 | 60 |
| 16 | 10 | 50 |
| 17 | 10 | 40 |
| 18 | 10 | 30 |
| 21 | 7 | 20 |
| TOTAL | 5 mins. | |

Control Circuits and Operation

Figure 2:
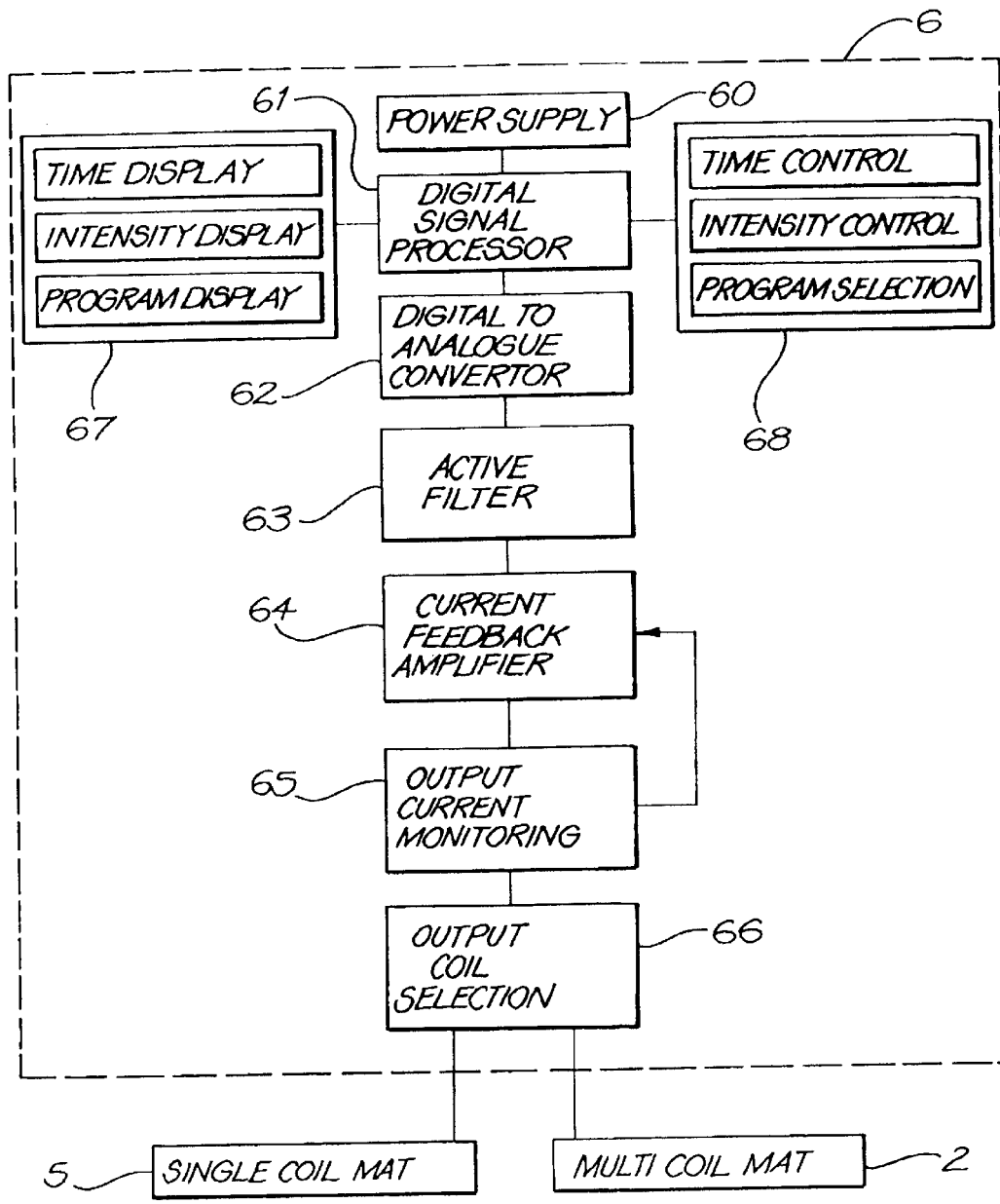
FIG. 2 is a schematic, functional block diagram of a power supply/control unit of the magnetic field therapy apparatus of FIG. 1.

Referring now to FIG. 2, the therapy control unit 6 is shown in functional block diagram form. The therapy control unit 6 includes a power supply 60, a digital signal processor (DSP) 61, a digital to analogue converter (DAC) 62, an active filter 63, a current feedback amplifier (CFA) 64, an output current monitoring unit 65, a coil selection unit 66, a display output unit 67, and a user selection input unit 68.

The power supply 60 provides a regulated d.c. output to enable operation of the other elements of the power supply/control unit 6, including a power circuit for driving the current feedback amplifier 64 which excites each of the induction coils.

The DSP 6b is programmed to digitally synthesise the therapy signal $V_{output}$ or $\mu_{AM}(t)$ as earlier discussed.

Preferably, each of the four high frequency signals $V_1$, $V_2$, $V_3$ and $V_4$ (which make up the basic signal), are generated with a sampling rate of 10 kHz and standardised to output a total power of 1W.

Each of these four high frequency signals $V_1$, $V_2$, $V_3$ and $V_4$ (which make up the basic signal, in superposition) can be described by the following equations:

$$V_1 = 300 \text{ Hz} = K_1 \sin(2\pi \times 300 \times t),$$
$$V_2 = 600 \text{ Hz} = K_2 \sin(2\pi \times 600 \times t),$$
$$V_3 = 800 \text{ Hz} = K_3 \sin(2\pi \times 800 \times t), \text{ and}$$
$$V_4 = 1{,}000 \text{ Hz} = K_4 \sin(2\pi \times 1{,}000 \times t).$$

where:

$K_n$ = amplitude scaling factor, each typically 0.8.

Next, the user signal $\mu_M(t)$ or $V_{var}$ can be described by the following equation:

$$V_{var} = (K_1 + K_2 + K_3 + K_4) \times (\text{ampfact}/100) \times (\sin(2\pi \times f_{var} \times t))$$

where:

ampfact = variable amplitude factor (%), and $f_{var}$ = required frequency of the user signal.

Finally, the therapy signal $\mu_{AM}(t)$ or $V_{output}$ is generated:

$$V_{output} = (V_1 + V_2 + V_3 + V_4 + V_{var}) \times K_o + \text{offset}$$

where:

offset = 0.1 to 3.5, nominally 0.25.

$K_o$ = a further scaling factor

These calculations can be performed by any convenient computer program, as would be apparent to one skilled in the art.

The amplitude modulated signal that is output from the DSP 61 is converted to an analogue equivalent by the DAC 62. The analogue signal that is output from the DAC 62 is input to the active filter 63 which removes unwanted frequencies, in particular those resulting from "noise". The filtered signal that is output from the DAC 62 is then processed by the current feedback amplifier 64 which makes adjustments to the rms value of current flow, as required to achieve the required intensity. The signal that is output from the CFA 64 is then monitored by the output current monitoring unit 65 and a feedback signal fed back to the CFA 64.

The therapy signal $\mu_{AM}(t)$ is input to the coil selection unit 66 which can selectively connect the therapy signal $\mu_{AM}(t)$ to either the multi-coil mat 2 or the single coil mat 5.

The DSP 61 is further connected to the display output unit 67 and the user control unit 68, both of which include a user interface panel 10.

Figure 3:
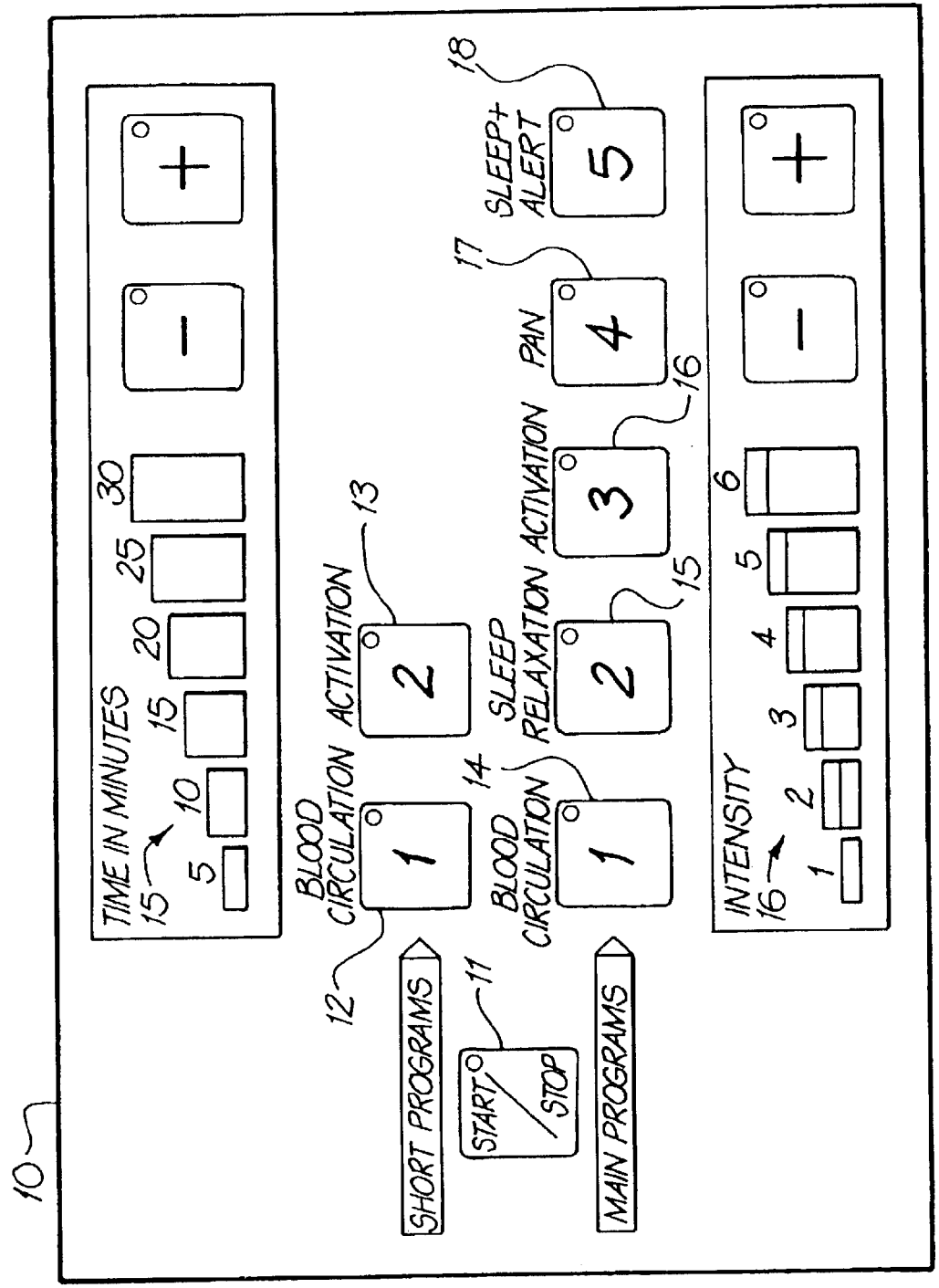
FIG. 3 is a layout for a user interface control panel for the magnetic field therapy apparatus of FIGS. 1 and 2.

Referring to FIG. 3, the user interface panel 10 includes the following:

(a) a start/stop selection button 11 and an associated status indicator 11a;

(b) program selection buttons 12, 13, 14, 15, 16, 17 & 18 and associated status indicators 12a, 13a, 14a, 15a, 16a, 17a & 18a, respectively;

(c) two time adjustment buttons 19 & 20 and associated status indicators 19a & 20a, respectively; and (d) two intensity adjustment buttons 21 & 22 and associated status indicators 21a & 22a.

The start/stop selection button 11 is actuable to turn the programs "on" or "off", the status of which is shown by indicator 11a. The program selection buttons 12, 13, 14, 15, 16, 17 & 18 and associated status indicators 12a, 13a, 14a, 15a, 16a, 17a & 18a are actuable to select any one of the available therapy programs. The time adjustment buttons 19 & 20 enable the user to selectively increase ("+") or decrease ("−") the duration of a therapy program from 5 to 30 minutes in six discrete steps of 5 minutes each. Similarly, the intensity adjustment buttons 21 & 22 enable the user to selectively increase ("+") or decrease ("−") the level of magnetic field intensity of a therapy program, within the range of 1.5 $\mu$T to 15 $\mu$T in six discrete steps. However, levels of up to 150 $\mu$T can be selected when the pain therapy program has been selected.

Figure 23:
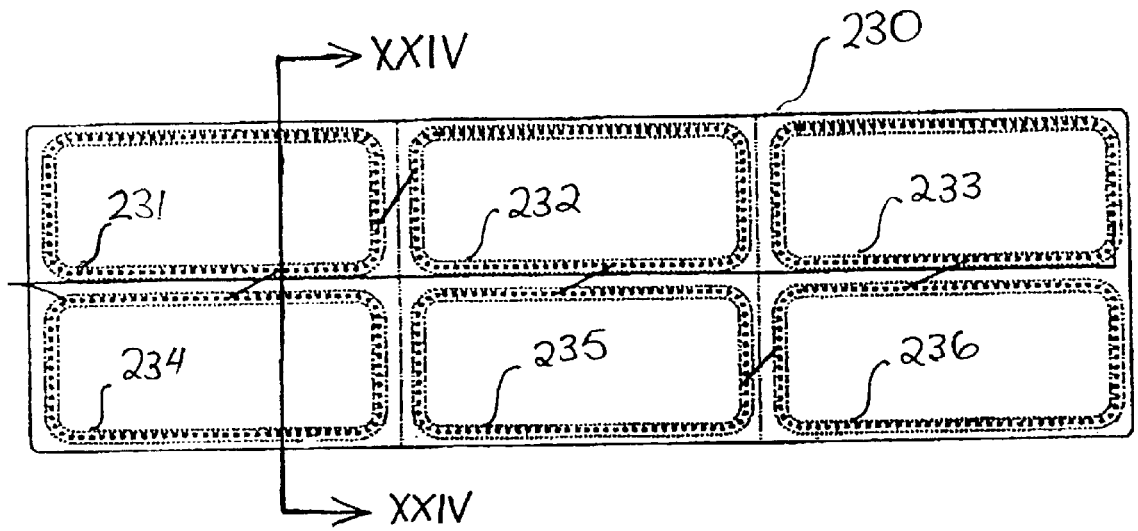
FIG. 23 is a schematic diagram of a multi-coil induction mat, according to an alternative embodiment.

Referring to FIG. 23, an alternative embodiment of the multi-coil induction mat 230 provides six, rectangular, flat, air-core induction coils 231–237, physically arranged as shown. This arrangement proportionally increases the magnetic field concentration that is produced in the longitudinal centre area of the mat 230. Therefore, a higher magnetic field concentration is directed to the spinal region of the user, which is thought to improve the overall effectiveness of the magnetic field treatment by activating important nerve cells of the body.

Figure 24:
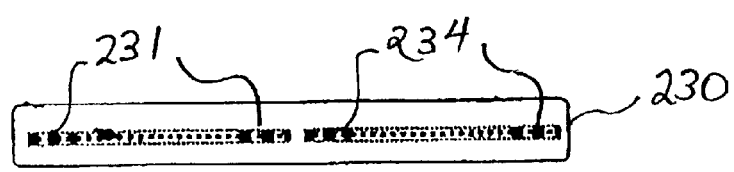
FIG. 24 is a cross sectional view of the multi-coil induction mat of FIG. 23.
Figure 25:
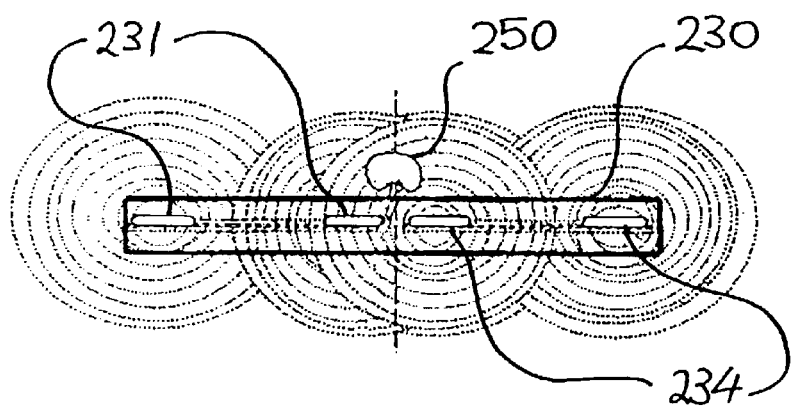
FIG. 25 is a representation of the multi-coil induction mat of FIG. 24, showing magnetic fields being produced during operation.

Referring now to FIG. 24, the multi-coil mat 230 of FIG. 23 is shown in cross-section along the lines XXIV—XXIV. FIG. 25 is the multi-coil mat 230 of FIG. 24, showing in phantom, expected magnetic fields produced during operation. Further, FIG. 25 shows an approximate position of the user's spinal cord 250 when undergoing therapy. The additive effect of adjacent coils along the longitudinal centre area of the mat 230 can provide around a 70% greater concentration of magnetic field to the spinal region of the user's body.

Referring back to FIGS. 1 and 2, a personal computer 7 can also be incorporated into the operation of the power supply/control unit 6 to provide patient and data management facilities for use in the context of a medical practice. These facilities can enabling storage of list/s of patients, entry of new patients including the creation of different files in accordance with anamnesis, automatic recording of therapy carried out for each patient including doctor's notes, printouts for accounting purposes and the like.

In an alternative embodiment, a negative ion generator can be incorporated into the operation of the magnetic field apparatus, so as to provide dual therapy.

Clinical Trials

Figure 17A:
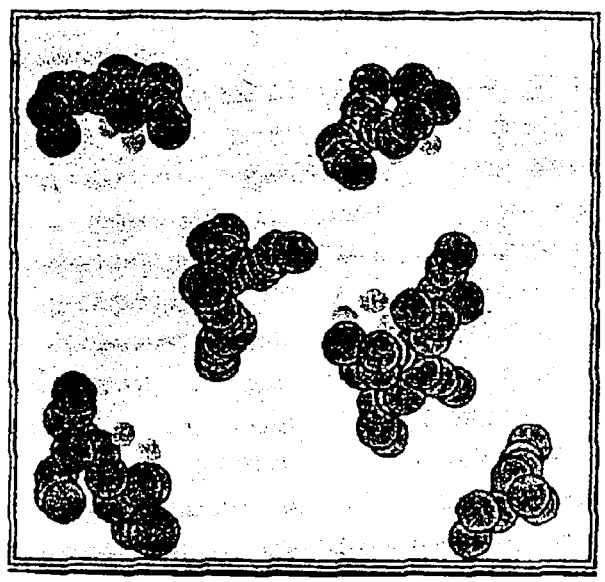
Figure 17B:
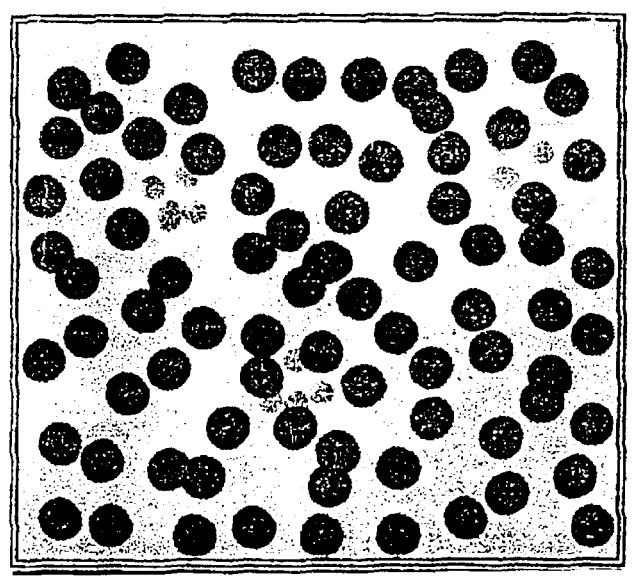

In confidential clinical trials utilising the 'Vitalisation/Blood Circulation' main program, a patient suffering from diabetes and extreme blood circulation problems in the legs was treated for 15 minutes. FIG. 17A shows a blood sample taken before the treatment, exhibiting the formation of 'rolls of coins' of red blood cells. Following the treatment, as shown in FIG. 17B, the red blood cells had desegregated, resulting in vastly improved blood flow for the patient. This, the inventor believes, leads to an improved state of the immune system and the amelioration of conditions associated with poor blood circulation. Particularly, blood pressure may be reduced and heart function improved.

Figure 18A:
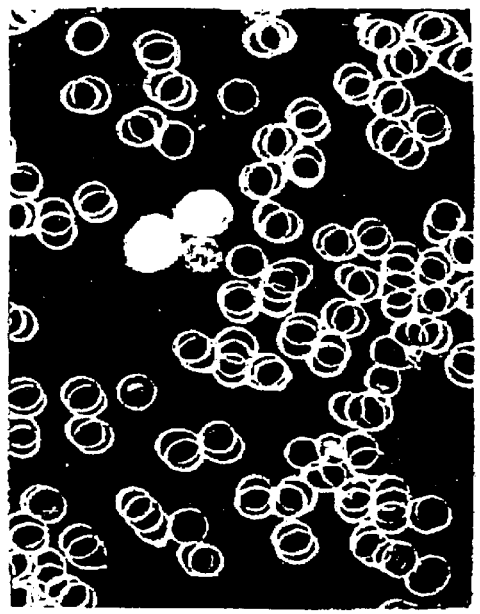
Figure 18B:
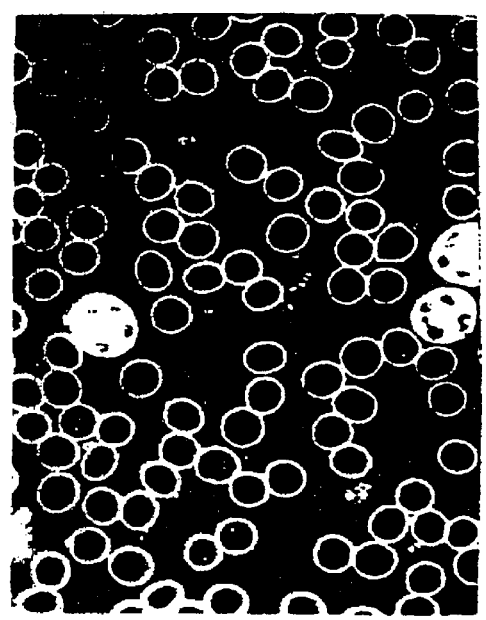
Figure 19A:
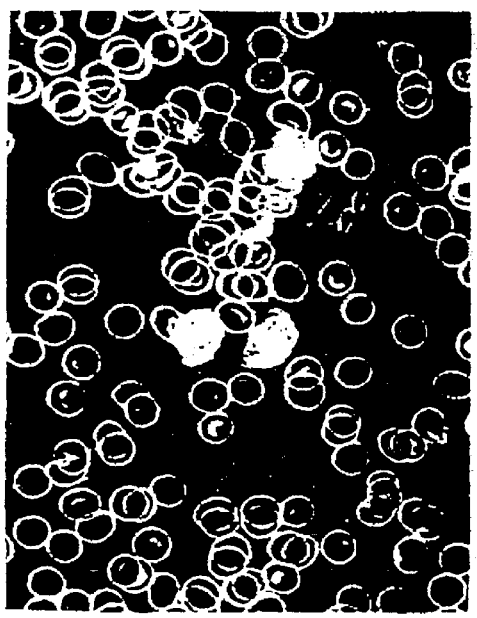
Figure 19B:
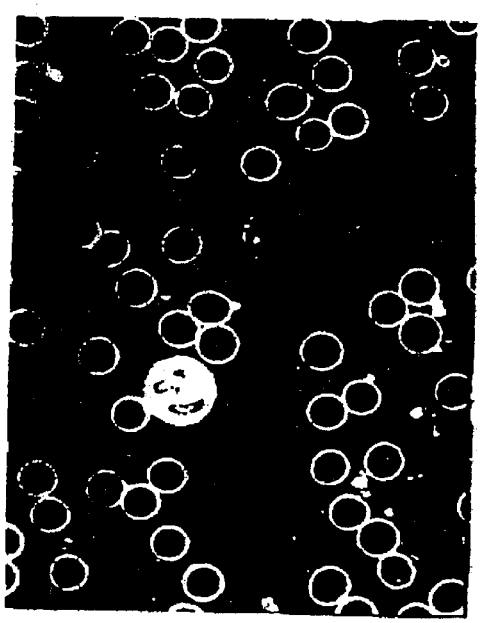

In other confidential clinical trials the treatment apparatus was utilised with patients suffering medical conditions, utilising the "circulation" program. Blood sample were taken from the patients before and after the treatment. FIGS. 18A and 18B show the red blood cells before and after treatment for a 40 year old cancer patient. FIGS. 19A and 19B show similar results for a 60 year old cancer patient. FIGS. 18A and 19A are the 'before treatment' blood samples, and FIGS. 18B and 19B are the 'after treatment' samples.

FIG. 20B shows the 'before treatment' blood sample for a 65 year old angina sufferer, with FIG. 20A showing the 'after treatment' sample.

Additionally, a 75 year old diabetic patient was treated, and FIG. 21B shows the 'before treatment' sample, with FIG. 21A showing the 'after treatment' sample.

Figure 22A:
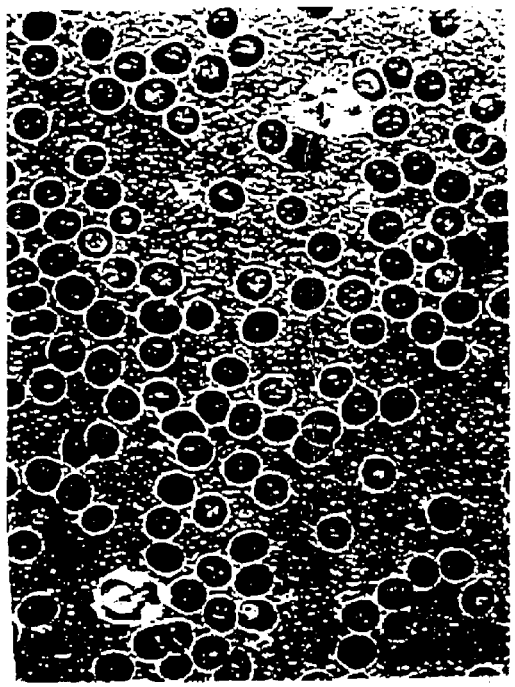
Figure 22B:
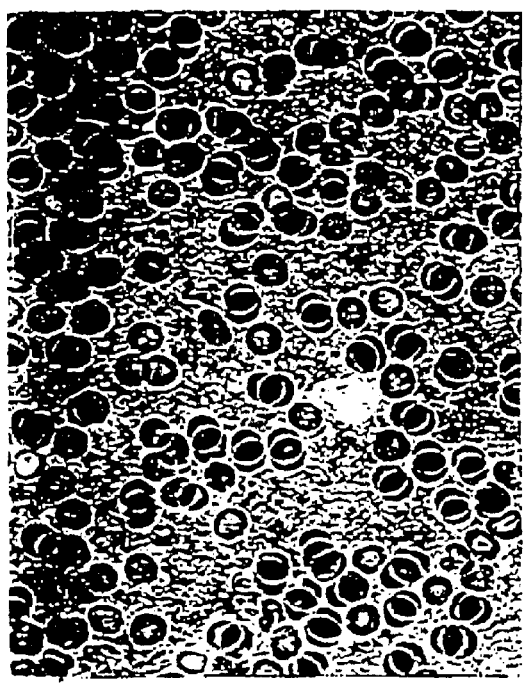

Finally, a 30 year old influenza sufferer was treated and, again, FIG. 22B shows the 'before treatment' sample and FIG. 22A shows the 'after treatment' sample.

The inventor believes that these blood tests provide evidence that some forms of cancer, angina, diabetes and influenza can be beneficially treated utilising the teaching of the invention. The treatment is in the nature of being temporarily amerliotaive, and not in the nature of a cure.

Industrial Applicability

It is apparent from the above that the embodiments of the invention are applicable to the medical electronics field.

I claim:

1. Apparatus for applying a therapeutic magnetic field to a biological entity, said apparatus comprising: a signal generation unit for generating an electrical treatment signal having a plurality of superimposed frequency components of approximately 300 Hz, 600 Hz, 800 Hz and 1,000 Hz., and an induction coil mat connected to said signal generation unit generating a magnetic field in accordance with said electrical signal.

2. Apparatus as claimed in claim 1, wherein said frequency components are fundamental frequencies.

3. Apparatus as claimed in claim 2, wherein said signal generation unit scales each component frequency of the treatment signal.

4. Apparatus as claimed in claim 3, wherein said further frequency components are chosen from one or more of approximately 2 Hz, 3 Hz, 4 Hz and 5 Hz.

5. Apparatus as claimed in claim 3, wherein said electrical treatment signal further includes one of more superimposed frequency components in a range between 2 Hz and 32 Hz.

6. Apparatus as claimed in claim 5, further comprising a user control unit generating user treatment settings provided to said signal generation unit, said user treatment settings corresponding to said further frequency components.

7. Apparatus as claimed in claim 5, wherein said signal generation unit applies a weighting factor to said further frequency components.

8. Apparatus as claimed in claim 7, wherein said signal generation unit controls the amplitude of the composite electrical treatment signal to restrict the average output intensity from the induction coil mat to less than 150 $\mu$T.

9. Apparatus as claimed in claim 1, wherein said induction coil mat includes at least two coils co-operatively arranged to increase magnetic field concentration in a region intended for a spinal area of a user.

10. Apparatus as claimed in claim 9, further comprising a negative ion generation means for simultaneous operation with said magnetic field.

11. A method for applying a therapeutic magnetic field to a biological entity, comprising the steps of:

generating a magnetic field having a plurality of superimposed frequency components of approximately 300 Hz, 600 Hz, 800 Hz and 1,000 Hz; and applying said magnetic field to said biological entity.

12. The method as claimed in claim 11, wherein said frequency components are fundamental frequencies.

13. The method as claimed in claim 12, wherein each component frequency of the treatment signal is scaled.

14. The method as claimed in claim 13, wherein said further frequency components are chosen from one or more of approximately 2 Hz, 3 Hz, 4 Hz and 5 Hz.

15. The method as claimed in claim 14, wherein the amplitude of the composite electrical treatment signal is controlled to restrict the average output intensity to less than 150 $\mu$T.

16. The method as claimed in claim 13, wherein said electrical treatment signal further includes one of more superimposed frequency components in a range between 2 Hz and 32 Hz.

17. The method as claimed in claim 16, wherein a weighting factor is applied to said further frequency components.

* * * * *